(12) United States Patent
Waineo

(10) Patent No.: US 12,161,244 B2
(45) Date of Patent: Dec. 10, 2024

(54) GLOVE-DISPENSING MEANS

(71) Applicant: Travis E. Waineo, Woodland, WA (US)

(72) Inventor: Travis E. Waineo, Woodland, WA (US)

( * ) Notice: Subject to any disclaimer, the term of this patent is extended or adjusted under 35 U.S.C. 154(b) by 428 days.

(21) Appl. No.: 17/583,780

(22) Filed: Jan. 25, 2022

(65) Prior Publication Data
US 2023/0033618 A1  Feb. 2, 2023

Related U.S. Application Data

(60) Provisional application No. 63/141,848, filed on Jan. 26, 2021.

(51) Int. Cl.
A61B 42/50 (2016.01)
A47G 25/90 (2006.01)
B65G 1/06 (2006.01)

(52) U.S. Cl.
CPC .............. *A47G 25/904* (2013.01); *B65G 1/06* (2013.01); *A61B 42/50* (2016.02)

(58) Field of Classification Search
CPC ................................ A47G 25/904; B65G 1/06
See application file for complete search history.

(56) References Cited

U.S. PATENT DOCUMENTS

| | | |
|---|---|---|
| 3,695,463 A | 10/1972 | Weisker et al. |
| 3,870,150 A | 3/1975 | Hummel |
| 4,002,276 A | 1/1977 | Poncy et al. |
| 4,155,494 A | 5/1979 | Poncy et al. |
| 4,275,812 A | 6/1981 | Poncy et al. |
| 4,889,266 A | 12/1989 | Wight |
| 4,909,413 A | 3/1990 | McCutcheon |
| 4,915,272 A | 4/1990 | Vlock |
| 5,058,785 A | 10/1991 | Rich et al. |
| 5,065,863 A | 11/1991 | Moyet-Ortiz |
| 5,878,909 A | 3/1999 | Rogow |
| 6,053,380 A | 4/2000 | Sherrod |
| 6,375,034 B1 | 4/2002 | Corbett |
| 6,932,253 B2 | 8/2005 | Sato |
| 6,953,130 B2 | 10/2005 | Corbett |
| 7,527,181 B1 | 5/2009 | Sullivan |
| 8,678,252 B2 | 3/2014 | Kelly et al. |
| 8,960,493 B1 | 2/2015 | Dennison et al. |
| 9,414,706 B2 | 8/2016 | Purcell et al. |
| 9,668,601 B1* | 6/2017 | Rogers .................... A61B 42/40 |
| 9,925,015 B2 | 3/2018 | Gravlee |
| 9,957,125 B2 | 5/2018 | Ray |
| 10,098,699 B1 | 10/2018 | Buck |
| 10,349,769 B2 | 7/2019 | Avshalom et al. |

(Continued)

OTHER PUBLICATIONS

AeroGlove, https://www.aeroglove.com/dispensers/, downloaded Feb. 18, 2022, first viewed Jan. 14, 2019.
Glove Assist—2016 Promotional Video—You Tube, https://www.youtube.com/watch?v=PmTFnSObgDU dated Apr. 13, 2016; downloaded Feb. 23, 2022.
PatentAuction.com An Automatic-Medical Glove Dispenser, https://www.patentauction.com/patent.php?nb=12363 downloaded Feb. 18, 2022.

(Continued)

*Primary Examiner* — Gene O Crawford
*Assistant Examiner* — Ayodeji T Ojofeitimi
(74) *Attorney, Agent, or Firm* — Enterprise Patent LLC

(57) ABSTRACT

A glove-dispensing system (120) may position glove cartridges (50) adjacent to glove portals (150) through which hands (190) can be inserted to don the gloves (20) that have been expanded. The glove-dispensing system (120) may dispense gloves (20) of different sizes in response to a size selection signal.

47 Claims, 20 Drawing Sheets

(56) References Cited

U.S. PATENT DOCUMENTS

| | | | |
|---|---|---|---|
| 10,512,516 | B1 | 12/2019 | Rogers et al. |
| 10,610,319 | B2 | 4/2020 | Backhaus et al. |
| 10,849,703 | B2 | 12/2020 | Backhaus et al. |
| 11,350,801 | B1* | 6/2022 | Dally .................... A47G 25/904 |
| 2011/0186589 | A1 | 8/2011 | Lee |
| 2015/0173546 | A1 | 6/2015 | Rogers et al. |
| 2016/0152403 | A1 | 6/2016 | Ray |
| 2016/0340068 | A1* | 11/2016 | Brandt Sanz ........ C11D 17/042 |
| 2017/0296281 | A1 | 10/2017 | Gaines et al. |
| 2019/0159619 | A1* | 5/2019 | Burk .................... A47G 25/904 |
| 2019/0167372 | A1* | 6/2019 | Backhaus ................ B65H 3/08 |
| 2021/0085412 | A1* | 3/2021 | Moghadam ............ A61B 42/50 |
| 2022/0233008 | A1* | 7/2022 | Waineo .................. A61B 42/50 |

OTHER PUBLICATIONS

Home—Glove Assist, Viewed Jan. 14th The Wayback Machine—https://web.archive.org/web/20190710001848/https://www.gloveassist.com/, downloaded Mar. 8, 2022.

Glove Tap, Hygienic Glove Applicator & Glove Donning Machine, Viewed Jan. 14, 2019, The Wayback Machine—https://web.archive.org/web/20190104174114/http://www.glovetap.com:80/home/, Downloaded Mar. 8, 2022.

Epsilon Patentability Search, May 7, 2020.

International Search Report of the EPO/ISA regarding corresponding International Application No. PCT/US2022/013687 (Apr. 7, 2022).

Written Opinion of the US/IPEA regarding corresponding International Application No. PCT/US2022/013687 (Feb. 7, 2023).

\* cited by examiner

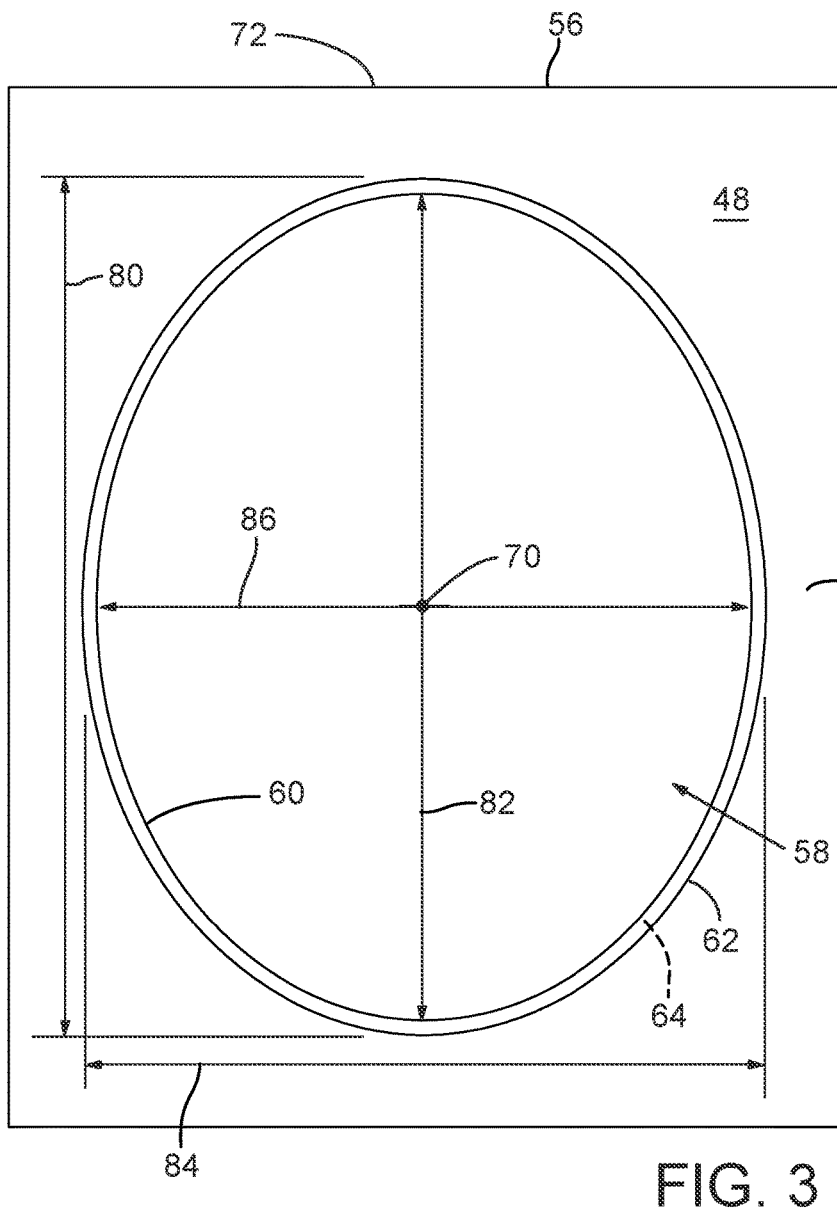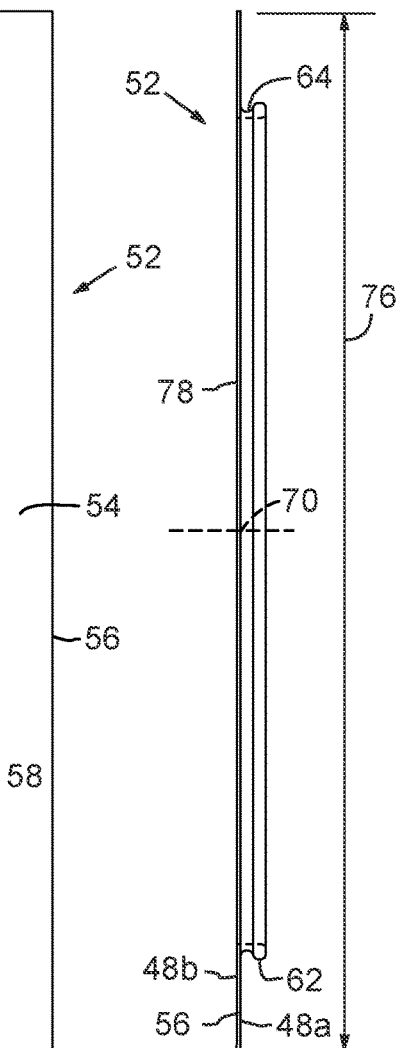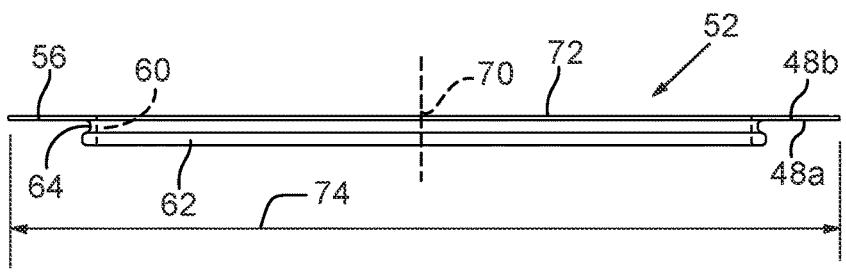
FIG. 3
FIG. 4
FIG. 5

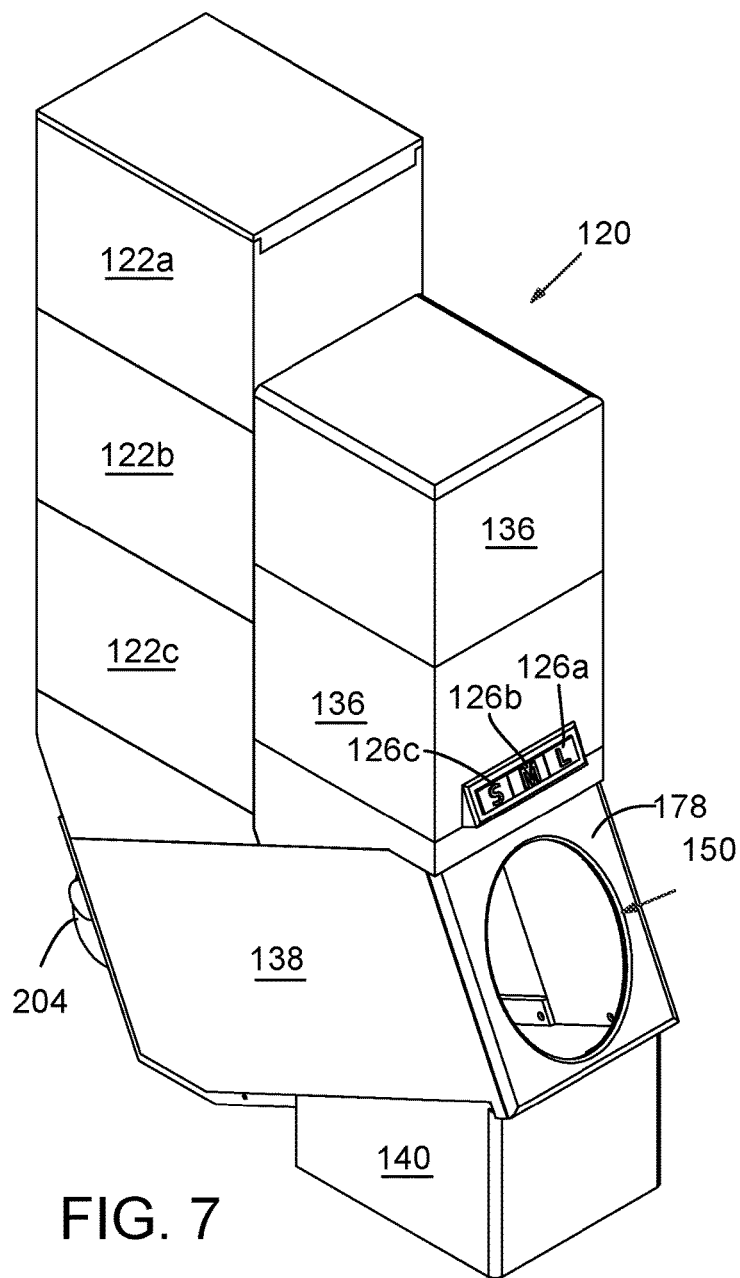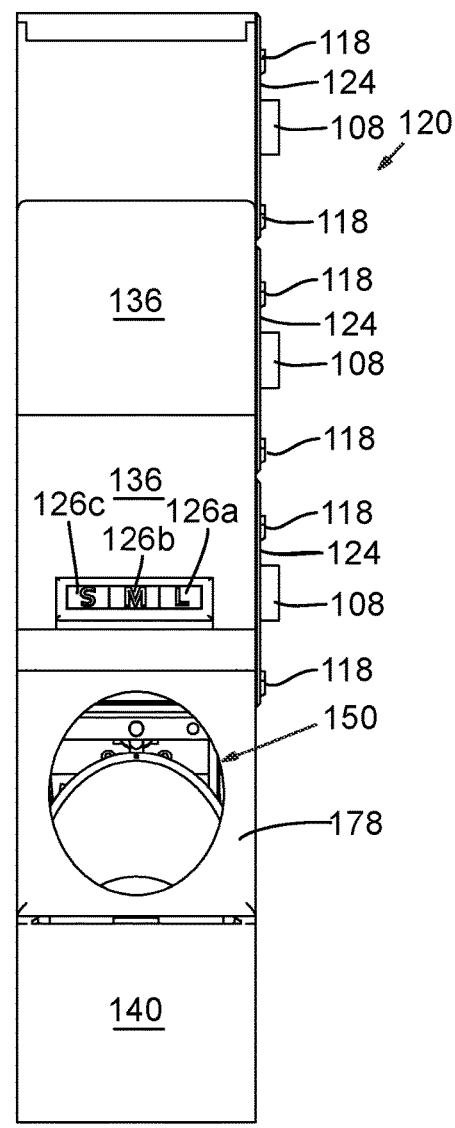

GLOVE-DISPENSING MEANS

CROSS REFERENCE TO RELATED APPLICATION

This application is a non-provisional application of U.S. Provisional Application No. 63/141,848, which was filed on Jan. 26, 2021, the contents of which are herein incorporated by reference in their entirety for all purposes.

TECHNICAL FIELD

The field of this disclosure relates generally to method and systems for glove dispensing and, in particular, to such methods and systems configured to utilize a glove cartridge.

BACKGROUND INFORMATION

Sanitary gloves have been an essential item for many industries for decades, including medical industries, food industries, and law enforcement agencies. These gloves can be relatively tight fitting and difficult or time consuming to put on, especially with damp hands that have just been washed. The gloves are often stored in boxes of 50 to 500 gloves, which are easy to contaminate while gloves are pulled from the box for use or for storage in after-market bins. Often only a single size of large gloves is available because the larger gloves are easier to put on and "fit" everyone. People with smaller hands are often compelled to use oversized gloves, which wastes material and may interfere with fine finger control.

Many devices have been made to facilitate and automate hygiene: automated water faucets, automated soap dispensers, automated paper towel dispensers, and automated hand dryers, for example. However, glove donning has not been automated in a practical manner.

OVERVIEW OF DISCLOSURE

One aspect of this disclosure relates to glove cartridges.

Another aspect of this disclosure relates to glove dispensing machines.

Yet another aspect of this disclosure relates to methods for dispensing gloves.

In some embodiments, a glove cartridge comprises: a flexible glove including an upper region, a middle region, and a lower region of glove material, wherein the upper region includes multiple finger parts, wherein the middle region includes a palm part and a back part, and wherein the lower region includes a wrist part and a glove base that defines a glove opening; and a cartridge including a cartridge frame having a cartridge boundary and a cartridge aperture, wherein the cartridge aperture defines an inner edge of the cartridge frame, and wherein the glove opening is positioned to extend around a majority of the cartridge aperture.

In some alternative, additional, or selectively cumulative embodiments, a glove cartridge comprises: a flexible glove including an upper region, a middle region, and a lower region of glove material, wherein the upper region includes multiple finger parts, wherein the middle region includes a palm part and a back part, and wherein the lower region includes a wrist part and a glove base that defines a glove opening; and a cartridge including a cartridge frame having a cartridge boundary and a cartridge aperture, wherein the cartridge aperture defines an inner edge, wherein the inner edge is in proximity to an aperture ridge that extends along at least a portion of the cartridge aperture, wherein the aperture ridge has a ridge base and a ridge lip, wherein the inner edge is closer to the ridge base than to the ridge lip, and wherein the glove base is positioned at the ridge base or between the ridge base and the ridge lip such that the glove opening is positioned about the cartridge aperture.

In some alternative, additional, or selectively cumulative embodiments, multiple glove cartridges including a first glove cartridge and a second glove cartridge comprise: a first flexible glove of the first glove cartridge including a first upper region, a first middle region, and a first lower region of glove material, wherein the first upper region includes multiple first finger parts, wherein the first middle region includes a first palm part and a first back part, and wherein the first lower region includes a first wrist part and a first glove base that defines a first glove opening; a first cartridge of the first glove cartridge including a first cartridge frame having a first cartridge boundary and a first cartridge aperture, wherein the first cartridge has a first cartridge boundary configuration, wherein the first cartridge aperture defines a first inner edge, wherein the first inner edge is in proximity to a first aperture ridge that extends along at least a first portion of the first cartridge aperture, wherein the first aperture ridge has a first ridge base and a first ridge lip, wherein the first inner edge is closer to the first ridge base than to the first ridge lip, and wherein the first glove base is positioned at the first ridge base or between the first ridge base and the first ridge lip such that the first glove opening is positioned about the first cartridge aperture; a second flexible glove of the second glove cartridge including a second upper region, a second middle region, and a second lower region of glove material, wherein the second upper region includes multiple second finger parts, wherein the second middle region includes a second palm part and a second back part, and wherein the second lower region includes a second wrist part and a second glove base that defines a second glove opening; and a second cartridge of the second glove cartridge including a second cartridge frame having a second cartridge boundary and a second cartridge aperture, wherein the second cartridge has a second cartridge boundary configuration that is different from the first cartridge boundary configuration, wherein the second cartridge aperture defines a second inner edge, wherein the second inner edge is in proximity to a second aperture ridge that extends along at least a second portion of the second cartridge aperture, wherein the second aperture ridge has a second ridge base and a second ridge lip, wherein the second inner edge is closer to the second ridge base than to the second ridge lip, and wherein the second glove base is positioned at the second ridge base or between the second ridge base and the second ridge lip such that the second glove opening is positioned about the second cartridge aperture.

In some alternative, additional, or selectively cumulative embodiments, an inventory of multiple glove cartridges including a first glove cartridge and a second glove cartridge comprises: a first flexible glove of the first glove cartridge including a first upper region, a first middle region, and a first lower region of glove material, wherein the first upper region includes multiple first finger parts, wherein the first middle region includes a first palm part and a first back part, and wherein the first lower region includes a first wrist part and a first glove base that defines a first glove opening; a first cartridge of the first glove cartridge including a first cartridge frame having a first cartridge boundary and a first cartridge aperture, wherein the first cartridge has a first cartridge boundary configuration, wherein the first cartridge aperture defines a first inner edge, wherein the first inner edge is in proximity to a first aperture ridge that extends along at least a first portion of the first cartridge aperture, wherein the first aperture ridge has a first ridge base and a first ridge lip, wherein the first inner edge is closer to the first ridge base than to the first ridge lip, and wherein the first glove base is positioned at the first ridge base or between the first ridge base and the first ridge lip such that the first glove opening is positioned about the first cartridge aperture; a second flexible glove of the second glove cartridge including a second upper region, a second middle region, and a second lower region of glove material, wherein the second upper region includes multiple second finger parts, wherein the second middle region includes a second palm part and a second back part, and wherein the second lower region includes a second wrist part and a second glove base that defines a second glove opening; and a second cartridge of the second glove cartridge including a second cartridge frame having a second cartridge boundary and a second cartridge aperture, wherein the second cartridge has a second cartridge feature that is different from a first cartridge feature of the first cartridge, wherein the second cartridge aperture defines a second inner edge, wherein the second inner edge is in proximity to a second aperture ridge that extends along at least a second portion of the second cartridge aperture, wherein the second aperture ridge has a second ridge base and a second ridge lip, wherein the second inner edge is closer to the second ridge base than to the second ridge lip, and wherein the second glove base is positioned at the second ridge base or between the second ridge base and the second ridge lip such that the second glove opening is positioned about the second cartridge aperture.

In some alternative, additional, or selectively cumulative embodiments, a glove-dispensing system comprises: a slot configured to receive a glove cartridge, the glove cartridge containing a glove attached around a cartridge aperture that is through a cartridge frame; a glove portal face having a rear surface; a glove portal configured to allow entry of a hand through the glove portal face and the rear surface; a sealing plate configured to apply a glove cartridge against the rear surface of the glove portal face such that glove portal overlaps the cartridge aperture; a vacuum chamber that includes the sealing plate; and a vacuum source in communication with the vacuum chamber.

In some alternative, additional, or selectively cumulative embodiments, a glove-dispensing system comprises: a holding chamber configured to house multiple glove cartridges, each of the glove cartridges containing a glove attached around a cartridge aperture that is through a cartridge frame; a glove portal face having a rear surface; a glove portal configured to allow entry of a hand through the glove portal face and the rear surface; a sealing plate configured to apply a glove cartridge against the rear surface of the glove portal face such that glove portal overlaps the cartridge aperture; a cartridge pathway chamber between the holding chamber and the sealing plate; a vacuum chamber that includes the sealing plate; and a vacuum source in communication with the vacuum chamber.

In some alternative, additional, or selectively cumulative embodiments, a glove-dispensing system comprises: a primary holding chamber configured to house primary multiple glove cartridges, each of the primary glove cartridges containing a primary glove attached around a primary cartridge aperture that is through a primary cartridge frame; a primary glove portal face having a primary rear surface; a primary glove portal configured to allow entry of a primary hand through the primary glove portal face and the primary rear surface; a primary sealing plate configured to apply a glove cartridge against the primary rear surface of the primary glove portal face such that primary glove portal overlaps the primary cartridge aperture; a primary cartridge pathway chamber between the primary holding chamber and the primary sealing plate; a primary vacuum chamber that includes the primary sealing plate; and a primary vacuum source in communication with the primary vacuum chamber; a secondary holding chamber configured to house secondary multiple glove cartridges each of the secondary glove cartridges containing a secondary glove attached around a secondary cartridge aperture that is through a secondary cartridge frame; a secondary glove portal face having a secondary rear surface; and a secondary glove portal configured to allow entry of a secondary hand through the secondary glove portal face and the secondary rear surface.

In some alternative, additional, or selectively cumulative embodiments, a glove-dispensing system comprises: a primary glove-dispending machine and a secondary glove-dispending machine, wherein the primary glove-dispending machine includes a primary holding chamber configured to house primary multiple glove cartridges each of the primary glove cartridges containing a primary glove attached around a primary cartridge aperture that is through a primary cartridge frame, a primary glove portal face having a primary rear surface, a primary glove portal configured to allow entry of a primary hand through the primary glove portal face and the primary rear surface, a primary sealing plate configured to apply a primary glove cartridge against the primary rear surface of the primary glove portal face such that primary glove portal overlaps the primary cartridge aperture, a primary cartridge pathway chamber between the primary holding chamber and the primary sealing plate, a primary vacuum chamber that includes the primary sealing plate, and a primary vacuum source in communication with the primary vacuum chamber, and wherein the secondary glove-dispensing machine, includes a secondary holding chamber configured to house secondary multiple glove cartridges each of the secondary glove cartridges containing a secondary glove attached around a secondary cartridge aperture that is through a secondary cartridge frame, a secondary glove portal face having a secondary rear surface, a secondary glove portal configured to allow entry of a secondary hand through the secondary glove portal face and the secondary rear surface, a secondary sealing plate configured to apply a secondary glove cartridge against the secondary rear surface of the secondary glove portal face such that secondary glove portal overlaps the secondary cartridge aperture, a secondary cartridge pathway chamber between the secondary holding chamber and the secondary sealing plate, a secondary vacuum chamber that includes the secondary sealing plate, and a secondary vacuum source in communication with the secondary vacuum chamber.

In some alternative, additional, or selectively cumulative embodiments, a method for facilitating the donning of a glove comprises: in response to a size selection signal, conveying from a holding chamber a glove cartridge so that it is positioned adjacent to a glove portal, wherein the glove cartridge contains a glove attached around a cartridge aperture through a cartridge frame, wherein the glove portal provides access to a vacuum chamber; applying vacuum pressure to the vacuum chamber to expand the glove into the vacuum chamber; and releasing the glove from the glove cartridge onto a hand in response to movement of the hand after it has been inserted into the glove or in response to positive pressure supplied to the vacuum chamber after the hand has been inserted into the glove.

In some alternative, additional, or selectively cumulative embodiments, a method for facilitating the donning gloves comprises: in response to a size selection signal, conveying from one or more holding chambers primary and secondary glove cartridges so that they are positioned adjacent to a common glove portal or to respective separate primary and secondary glove portals, wherein the primary glove cartridge contains a primary glove attached around a primary cartridge aperture through a primary cartridge frame, wherein the secondary glove cartridge contains a secondary glove attached around a secondary cartridge aperture through a secondary cartridge frame, wherein the common glove portal or the respective separate primary and secondary glove portals provide access to a common vacuum chamber or to respective separate primary and secondary vacuum chambers; applying vacuum pressure to the common vacuum chamber or to the respective separate primary and secondary vacuum chambers to expand the primary and secondary gloves into the common vacuum chamber or into the respective separate primary and secondary vacuum chambers; and releasing the primary and secondary gloves from the respective primary and secondary glove cartridges onto primary and secondary hands in response to positive pressure supplied to the vacuum chamber or to the respective separate primary and secondary vacuum chambers after the primary and secondary hands have been inserted into the respective primary and secondary gloves, or in response to movement of the primary and secondary hands after they have been inserted into the respective primary and secondary gloves, or in response to both positive pressure supplied to the vacuum chamber or to the respective separate primary and secondary vacuum chambers and movement of the primary and secondary hands after they have been inserted into the respective primary and secondary gloves.

In some alternative, additional, or selectively cumulative embodiments, the glove opening is positioned to extend around all of the cartridge aperture.

In some alternative, additional, or selectively cumulative embodiments, the inner edge is in proximity to an aperture ridge that extends along at least a portion of the cartridge aperture, the aperture ridge has a ridge base and a ridge lip, the inner edge is closer to the ridge base than to the ridge lip, and the glove base is positioned at the ridge base or between the ridge base and the ridge lip such that the glove opening is positioned around the cartridge aperture.

In some alternative, additional, or selectively cumulative embodiments, the glove cartridge is configured to facilitate formation of a vacuum seal around a glove portal into a vacuum chamber.

In some alternative, additional, or selectively cumulative embodiments, the cartridge boundary defines a cartridge dimensional area, the inner edge defines a cartridge aperture dimensional area, and the cartridge aperture dimensional area is greater than or equal to the cartridge dimensional area.

In some alternative, additional, or selectively cumulative embodiments, a cartridge major surface between the cartridge boundary and the inner edge, wherein the cartridge major surface is configured to facilitate formation of a vacuum seal around a glove portal into a vacuum chamber.

In some alternative, additional, or selectively cumulative embodiments, the multiple finger parts include a thumb part that has a different shape than that of the other finger parts.

In some alternative, additional, or selectively cumulative embodiments, the glove comprises a nitrile material.

In some alternative, additional, or selectively cumulative embodiments, the glove comprises a vinyl material.

In some alternative, additional, or selectively cumulative embodiments, the glove comprises latex.

In some alternative, additional, or selectively cumulative embodiments, the glove comprises a polymer material.

In some alternative, additional, or selectively cumulative embodiments, the glove base includes a glove lip that includes a thicker region of glove material.

In some alternative, additional, or selectively cumulative embodiments, the cartridge frame has a boundary shape resembling a polygon.

In some alternative, additional, or selectively cumulative embodiments, the cartridge frame has a boundary shape resembling a rectangle, square, ellipse, circle, or oval.

In some alternative, additional, or selectively cumulative embodiments, the cartridge aperture has an aperture shape resembling a polygon.

In some alternative, additional, or selectively cumulative embodiments, the cartridge aperture has an aperture shape resembling a rectangle, square, ellipse, circle, or oval.

In some alternative, additional, or selectively cumulative embodiments, the glove base has a glove major axis and a glove minor axis that is transverse to the glove major axis, wherein the cartridge aperture has an aperture major axis and an aperture minor axis that is transverse to the aperture major axis, and wherein the glove is positioned about the cartridge aperture such that the glove major axis is substantially parallel to the aperture major axis.

In some alternative, additional, or selectively cumulative embodiments, the cartridge has a major cartridge surface between the cartridge boundary and the cartridge aperture.

In some alternative, additional, or selectively cumulative embodiments, the cartridge has a major cartridge surface between the cartridge boundary and the cartridge aperture, wherein the cartridge boundary has a boundary wall that is transverse to the major cartridge surface.

In some alternative, additional, or selectively cumulative embodiments, the boundary wall tapers externally as it extends away from the major cartridge surface.

In some alternative, additional, or selectively cumulative embodiments, the cartridge has a front side and a rear side, and wherein the front side is configured for entry of a hand into the glove.

In some alternative, additional, or selectively cumulative embodiments, the cartridge is configured to be stackable with multiple additional cartridges having similar features.

In some alternative, additional, or selectively cumulative embodiments, the cartridge has a major cartridge surface between the cartridge boundary and the cartridge aperture, wherein the cartridge is configured to be stackable with multiple additional cartridges having similar features, such that major cartridge surfaces of the multiple additional cartridges are substantially parallel when they are in a stacked configuration.

In some alternative, additional, or selectively cumulative embodiments, the cartridge has a front side and a rear side, and wherein the front side is configured to provide a receptacle for the rear side of an additional cartridge having similar features.

In some alternative, additional, or selectively cumulative embodiments, the cartridge has a major cartridge surface between the cartridge boundary and the cartridge aperture, wherein the cartridge boundary has a boundary wall that is transverse to the major cartridge surface, wherein the cartridge has a front side and a rear side, wherein the boundary wall extends from the front side, and wherein the front side is configured to provide a receptacle for the rear side of an additional cartridge having similar features.

In some alternative, additional, or selectively cumulative embodiments, the aperture ridge extends along at least a major portion of the cartridge aperture.

In some alternative, additional, or selectively cumulative embodiments, the aperture ridge extends along the entire inner edge of the cartridge aperture.

In some alternative, additional, or selectively cumulative embodiments, the aperture ridge is continuous.

In some alternative, additional, or selectively cumulative embodiments, the aperture ridge is discontinuous.

In some alternative, additional, or selectively cumulative embodiments, the cartridge is configured to hold the glove during the donning process.

In some alternative, additional, or selectively cumulative embodiments, the cartridge has a front side and a rear side that is opposite the front side, wherein the cartridge comprises a rear protective layer that is attached to the cartridge and covers the cartridge aperture on the rear side of the cartridge such that the rear protective layer is configured to prevent external contact with the glove from the rear side of the cartridge aperture.

In some alternative, additional, or selectively cumulative embodiments, the rear protective layer is a bag configured to accommodate a major portion of the glove when it is inflated.

In some alternative, additional, or selectively cumulative embodiments, the cartridge has a front side and a rear side, and wherein the cartridge comprises a front protective layer that at least partly occludes the cartridge aperture on the front side of the cartridge.

In some alternative, additional, or selectively cumulative embodiments, the front protective layer is configured to break during a glove donning or glove extraction process.

In some alternative, additional, or selectively cumulative embodiments, the front protective layer has one or more weakened break-lines.

In some alternative, additional, or selectively cumulative embodiments, the one or more weakened break-lines are perforated.

In some alternative, additional, or selectively cumulative embodiments, the front protective layer has an open central portal.

In some alternative, additional, or selectively cumulative embodiments, the cartridge comprises a front protective layer that at least partly occludes the cartridge aperture on the front side of the cartridge, wherein the cartridge has a rear side that is opposite the front side, wherein the cartridge comprises a rear protective layer that is attached to the cartridge and covers the cartridge aperture on the rear side of the cartridge, wherein a major portion of the glove is positioned between a plane of the front protective layer and the rear protective layer and within a volume of the cartridge aperture therebetween.

In some alternative, additional, or selectively cumulative embodiments, the cartridge has a front side and a rear side, and wherein the aperture ridge is positioned on a front side of the cartridge.

In some alternative, additional, or selectively cumulative embodiments, the cartridge has a major axis that is smaller than 155 mm.

In some alternative, additional, or selectively cumulative embodiments, the cartridge is disposable.

In some alternative, additional, or selectively cumulative embodiments, the cartridge is reusable.

In some alternative, additional, or selectively cumulative embodiments, the cartridge is recyclable.

In some alternative, additional, or selectively cumulative embodiments, the cartridge is biodegradable.

In some alternative, additional, or selectively cumulative embodiments, the ridge base has a base perimeter that is smaller than a lip perimeter of the ridge lip.

In some alternative, additional, or selectively cumulative embodiments, space between the cartridge boundary and the inner edge defines a cartridge surface area, wherein the inner edge defines a cartridge aperture dimensional area, and wherein the cartridge aperture dimensional area is greater than or equal to the cartridge surface area.

In some alternative, additional, or selectively cumulative embodiments, the cartridge has a major cartridge surface between the cartridge boundary and the cartridge aperture, and wherein the major cartridge surface is substantially flat.

In some alternative, additional, or selectively cumulative embodiments, the cartridge has a major cartridge surface between the cartridge boundary and the cartridge aperture, and wherein the major cartridge surface is configured to form a seal against a flat surface.

In some alternative, additional, or selectively cumulative embodiments, the cartridge boundary has multiple sides edges, including first and second side edges, wherein the first side edge has a first edge dimension configured to fit within a doorway dimension of holding chamber configured to store multiple cartridges, and wherein the second side edge has a second edge dimension that is larger than the first edge dimension and larger than the doorway dimension. In some alternative, additional, or selectively cumulative embodiments, the first and second edge dimensions facilitate placement of the glove cartridge in a selected orientation into a holding chamber.

In some alternative, additional, or selectively cumulative embodiments, the cartridge boundary has at least one perimeter edge having one or more notches or one or more outward tabs.

In some alternative, additional, or selectively cumulative embodiments, the cartridge boundary has at least one perimeter edge having one or more notches or one or more outward tabs that are mated to features along a wall of holding chamber configured to store multiple cartridges.

In some alternative, additional, or selectively cumulative embodiments, the cartridge boundary has multiple sides edges, including first and second side edges, wherein the first side edge has a first edge configuration that correlates with a first wall feature of a holding chamber configured to store multiple cartridges, wherein the second side edge has a second edge configuration that is different from the first edge configuration, such that the second edge configuration is incompatible with the first wall feature.

In some alternative, additional, or selectively cumulative embodiments, the first and second edge configurations are different with respect to one or more of: size, shape, color, notch, and tab.

In some alternative, additional, or selectively cumulative embodiments, the first and second edge configurations facilitate placement of the glove cartridge in a selected orientation into the holding chamber.

In some alternative, additional, or selectively cumulative embodiments, an additional flexible glove includes an additional upper region, an additional middle region, and an additional lower region of glove material, wherein the additional upper region includes additional multiple finger parts, wherein the additional middle region includes an additional palm part and an additional back part, and wherein the additional lower region includes an additional wrist part and an additional glove base that defines an additional glove opening; and an additional cartridge aperture defines an additional inner edge, wherein the additional inner edge is in proximity to an additional aperture ridge that extends along at least an additional portion of the additional cartridge aperture, wherein the additional aperture ridge has an additional ridge base and an additional ridge lip, wherein the additional inner edge is closer to the additional ridge base than to the additional ridge lip, and wherein the additional glove base is positioned at the additional ridge base or between the additional ridge base and the additional ridge lip such that the additional glove opening is positioned about the additional cartridge aperture.

In some alternative, additional, or selectively cumulative embodiments, the aperture and the additional aperture lie in substantially the same plane.

In some alternative, additional, or selectively cumulative embodiments, the aperture and the additional aperture lie in different planes.

In some alternative, additional, or selectively cumulative embodiments, the cartridge has a major surface between the cartridge frame boundary and the cartridge aperture, and wherein the major surface comprises cardboard, metal, or plastic.

In some alternative, additional, or selectively cumulative embodiments, the cartridge has a major surface between the cartridge frame boundary and the cartridge aperture, and wherein the major surface comprises a transparent, partly-transparent, or translucent material.

In some alternative, additional, or selectively cumulative embodiments, the first and second cartridge boundary configurations are different with respect to one or more of: size, shape, color, notch, and tab.

In some alternative, additional, or selectively cumulative embodiments, the first and second cartridge boundary configurations are configured to facilitate placement into different holding chambers, including first and second holding chambers having respective first and second chamber features correlated with the respective first and second cartridge boundary configuration, such that first holding chamber is configured to house first glove cartridges and the second holding chamber is configured to house second glove cartridges.

In some alternative, additional, or selectively cumulative embodiments, the glove-dispensing system comprises one or more holding chambers configured to house multiple glove cartridges, each of the glove cartridges containing a glove attached around a cartridge aperture that is through a cartridge frame.

In some alternative, additional, or selectively cumulative embodiments, the glove-dispensing system comprises a cartridge pathway chamber between the holding chamber and the sealing plate.

In some alternative, additional, or selectively cumulative embodiments, the glove-dispensing system comprises multiple holding chambers.

In some alternative, additional, or selectively cumulative embodiments, the glove-dispensing system comprises multiple holding chambers, including first and second holding chambers of different sizes.

In some alternative, additional, or selectively cumulative embodiments, the glove-dispensing system comprises multiple holding chambers, including first and second holding chambers configured for holding glove cartridges containing different sizes of gloves.

In some alternative, additional, or selectively cumulative embodiments, the glove-dispensing system comprises multiple holding chambers, including first and second holding chambers, wherein the first holding chamber has a first feature that correlates with a first edge configuration of a first side edge of a first glove cartridge, wherein the second holding chamber has a second feature that correlates with a second edge configuration of a second side edge of a second glove cartridge, wherein the first feature of the first holding chamber is different from the second feature of the second holding chamber, wherein the first edge configuration of the first glove cartridge is different from the second edge configuration of the second glove cartridge, such that the first holding chamber is incompatible with the second glove cartridge.

In some alternative, additional, or selectively cumulative embodiments, the glove-dispensing system comprises multiple holding chambers, including first and second holding chambers, wherein the first holding chamber has a first wall feature that correlates with a first edge configuration of a first side edge of a first glove cartridge, and wherein the first wall feature is incompatible with a second edge configuration of a second side edge of the first glove cartridge.

In some alternative, additional, or selectively cumulative embodiments, the first and second edge configurations are different with respect to one or more of: size, shape, color, notch, and tab.

In some alternative, additional, or selectively cumulative embodiments, the glove-dispensing system comprises a cartridge deck actuator that is operable to move a glove cartridge to the cartridge pathway chamber.

In some alternative, additional, or selectively cumulative embodiments, the glove-dispensing system comprises a glove size-selector mechanism that presents indicators of different glove sizes, including first and second glove sizes, that are available for selection, wherein the glove size-selector mechanism is configured to directly or indirectly communicate with a cartridge deck actuator that is operable to move a glove cartridge that contains a glove of a selected size to the cartridge pathway chamber.

In some alternative, additional, or selectively cumulative embodiments, the glove portal has a glove portal area that is greater than or equal to a cartridge aperture area of the cartridge aperture.

In some alternative, additional, or selectively cumulative embodiments, the sealing plate has a sealing plate aperture that is configured to be aligned with the glove portal whenever the sealing plate is employed to apply the glove cartridge against the rear surface of the glove portal face, wherein the sealing plate aperture is configured to allow entry of a hand through the sealing plate.

In some alternative, additional, or selectively cumulative embodiments, the glove-dispensing system comprises a sealing plate actuator that is configured to apply force to the sealing plate to move a glove cartridge on the sealing plate toward the rear surface of the glove portal face.

In some alternative, additional, or selectively cumulative embodiments, the holding chamber is configured to hold glove cartridges in a first orientation, wherein the cartridge pathway chamber is configured to retain the first orientation of the glove cartridge.

In some alternative, additional, or selectively cumulative embodiments, the holding chamber is configured to hold glove cartridges in a first orientation, wherein the cartridge pathway chamber is configured to change the first orientation of the glove cartridge to a second orientation that is different from the first orientation.

In some alternative, additional, or selectively cumulative embodiments, the glove portal face is transparent, partly transparent, or translucent.

In some alternative, additional, or selectively cumulative embodiments, the holding chamber is a primary holding chamber, wherein the glove portal face is a primary glove portal face, wherein the glove portal is a primary glove portal, wherein the sealing plate is a primary sealing plate, wherein the cartridge pathway chamber is a primary cartridge pathway chamber, wherein the vacuum chamber is a primary vacuum chamber, and wherein the vacuum source is a primary vacuum source, and wherein the glove-dispensing system further comprises one of more of a secondary holding chamber, a secondary glove portal face, a secondary glove portal, a secondary sealing plate, a secondary cartridge pathway chamber, a secondary vacuum chamber, and a secondary vacuum source.

In some alternative, additional, or selectively cumulative embodiments, the holding chamber is a primary holding chamber, wherein the glove portal face is a primary glove portal face, wherein the glove portal is a primary glove portal, wherein the sealing plate is a primary sealing plate, wherein the cartridge pathway chamber is a primary cartridge pathway chamber, wherein the vacuum chamber is a primary vacuum chamber, wherein the vacuum source is a primary vacuum source, and wherein the glove-dispensing system further comprises a secondary glove portal, wherein the glove-dispensing system is configured to provide a primary glove cartridge containing a primary glove in a primary glove orientation at the primary glove portal, wherein the glove-dispensing system is configured to provide a secondary glove cartridge containing a secondary glove in a secondary glove orientation at the secondary glove portal, and wherein the primary and secondary glove orientations are different.

In some alternative, additional, or selectively cumulative embodiments, the glove-dispensing system comprises a secondary holding chamber, wherein the primary and secondary holding chambers are configured for holding respective primary and secondary glove cartridges containing gloves of the same size.

In some alternative, additional, or selectively cumulative embodiments, the glove-dispensing system comprises a secondary vacuum chamber, wherein the secondary vacuum chamber is connected to the secondary glove portal, and wherein the primary vacuum chamber is connected to the primary glove portal.

In some alternative, additional, or selectively cumulative embodiments, the vacuum source is connected to the primary and secondary vacuum chambers.

In some alternative, additional, or selectively cumulative embodiments, the glove-dispensing system comprises a secondary vacuum source that is connected to the secondary vacuum chamber, and wherein the primary vacuum source is connected to the primary vacuum chamber.

In some alternative, additional, or selectively cumulative embodiments, the holding chamber is a primary holding chamber, wherein the glove portal face is a primary glove portal face, wherein the glove portal is a primary glove portal, wherein the sealing plate is a primary sealing plate, wherein the cartridge pathway chamber is a primary cartridge pathway chamber, wherein the vacuum chamber is a primary vacuum chamber, wherein the vacuum source is a primary vacuum source, and wherein the glove-dispensing system further comprises a secondary holding chamber, a secondary glove portal face, a secondary glove portal, a second sealing plate, a secondary cartridge pathway chamber, a secondary vacuum chamber, and a secondary vacuum source.

In some alternative, additional, or selectively cumulative embodiments, the glove-dispensing system is configured to be mounted on a wall.

In some alternative, additional, or selectively cumulative embodiments, the glove-dispensing system is configured to be mounted on a wall without additional support from a ground surface and/or such that the glove-dispensing system does not reach the floor.

In some alternative, additional, or selectively cumulative embodiments, the vacuum chamber is configured to accommodate positive pressure.

In some alternative, additional, or selectively cumulative embodiments, the vacuum source is configurable to provide positive pressure.

In some alternative, additional, or selectively cumulative embodiments, the vacuum chamber is connected to a source of positive pressure.

In some alternative, additional, or selectively cumulative embodiments, the glove portal face is a primary glove portal face, and wherein the glove portal is a primary glove portal, wherein the glove-dispensing system further comprises a secondary glove portal that is through a secondary glove portal face, wherein the secondary glove portal face lies in a secondary plane that is different from primary plane of the primary glove portal face.

In some alternative, additional, or selectively cumulative embodiments, the glove cartridges are primary glove cartridges, wherein the glove is a primary glove, wherein the cartridge aperture is a primary cartridge aperture, wherein the cartridge frame is a primary cartridge frame, wherein the glove portal is a primary glove portal that is through a primary portal face and a primary back surface of the primary portal face, wherein the glove-dispensing system further comprises: a secondary glove portal that is through a secondary portal face and a secondary back surface of the secondary portal face; and secondary glove cartridges, each of the glove cartridges containing a secondary glove attached around a secondary cartridge aperture that is through a secondary cartridge frame, wherein the primary glove has a primary major opening axis, wherein the secondary glove has a secondary major opening axis, wherein the primary cartridge aperture has a primary aperture axis, wherein the secondary cartridge aperture has a secondary aperture axis, wherein the primary major opening axis has a primary relationship with the primary aperture axis, wherein the secondary major opening axis has a secondary relationship with the secondary aperture axis, and wherein the glove-dispensing system in cooperation with the primary and secondary relationships is configured to apply the primary and secondary glove cartridges to the respective primary and secondary back surfaces of the respective primary and secondary glove portal faces so that the primary major opening axis is transverse to the secondary major opening axis.

In some alternative, additional, or selectively cumulative embodiments, the primary glove cartridge has a primary cartridge boundary with a primary side edge, wherein the secondary glove cartridge has a secondary cartridge boundary with a secondary side edge, and wherein the primary side edge and the secondary side edge are nonparallel.

In some alternative, additional, or selectively cumulative embodiments, the secondary sealing plate is configured to apply a secondary glove cartridge against the secondary rear surface of the secondary glove portal face such that secondary glove portal overlaps the secondary cartridge aperture, the primary cartridge pathway chamber is positioned between the secondary holding chamber and the secondary sealing plate, the primary vacuum chamber includes the secondary sealing plate, and/or the primary vacuum source is in communication with the second vacuum chamber.

In some alternative, additional, or selectively cumulative embodiments, the vacuum source is configured to cooperate with the vacuum chamber and a glove cartridge to inflate a glove on the glove cartridge.

In some alternative, additional, or selectively cumulative embodiments, the vacuum source is configured to cooperate with the vacuum chamber and a glove cartridge to stretch at least one finger part of the glove on the glove cartridge.

In some alternative, additional, or selectively cumulative embodiments, the vacuum source is configured to cooperate with the vacuum chamber and a glove cartridge to stretch multiple finger parts of the glove on the glove cartridge.

In some alternative, additional, or selectively cumulative embodiments, the vacuum source is configured to cooperate with the vacuum chamber and a glove cartridge to stretch a middle region of the glove on the glove cartridge.

In some alternative, additional, or selectively cumulative embodiments, applying vacuum pressure causes inflation of the glove on the glove cartridge.

In some alternative, additional, or selectively cumulative embodiments, applying vacuum pressure causes stretching of at least one finger part of the glove on the glove cartridge.

In some alternative, additional, or selectively cumulative embodiments, applying vacuum pressure causes stretching of multiple finger parts of the glove on the glove cartridge.

In some alternative, additional, or selectively cumulative embodiments, applying vacuum pressure causes stretching of a middle region of the glove on the glove cartridge.

Selectively cumulative embodiments are embodiments that include any combination of multiple embodiments that are not mutually exclusive.

Additional aspects and advantages will be apparent from the following detailed description of example embodiments, which proceeds with reference to the accompanying drawings.

BRIEF DESCRIPTION OF THE DRAWINGS

FIG. 3 is a front view of a cartridge without a glove.

FIG. 4 is a right side view or left side view of the cartridge.

FIG. 5 is a top view or a bottom view of the cartridge.

FIG. 7 is a left front isometric view of a glove-dispensing machine equipped with a stack of glove cartridges.

FIG. 8 is front view of a glove-dispensing machine.

DETAILED DESCRIPTION OF EMBODIMENTS

Figure 1:
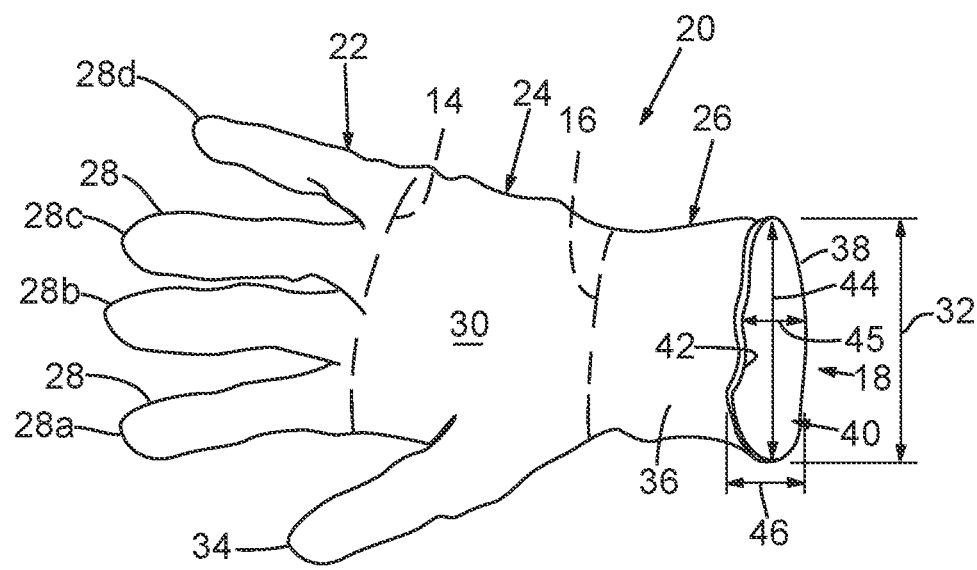
FIG. 1 is a front view of a conventional flexible glove.

Example embodiments are described below with reference to the accompanying drawings. Unless otherwise expressly stated in the drawings, the sizes, positions, etc., of components, features, elements, etc., as well as any distances therebetween, are not necessarily to scale, and may be disproportionate and/or exaggerated for clarity.

The terminology used herein is for the purpose of describing particular example embodiments only and is not intended to be limiting. As used herein, the singular forms "a," "an" and "the" are intended to include the plural forms as well, unless the context clearly indicates otherwise. It should be recognized that the terms "comprise," "comprises," "comprising," "includes," "include," "including,"

"have," "has," and having" when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween. Unless indicated otherwise, terms such as "first," "second," etc., are only used to distinguish one element from another. For example, one element could be termed a "first element" and similarly, another element could be termed a "second element," or vice versa. The section headings used herein are for organizational purposes only and are not to be construed as limiting the subject matter described.

Unless indicated otherwise, the terms "about," "thereabout," "substantially," etc. mean that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art.

Spatially relative terms, such as "right," left," "below," "beneath," "lower," "above," and "upper," and the like, may be used herein for ease of description to describe one element's or feature's relationship to another element or feature, as illustrated in the drawings. It should be recognized that the spatially relative terms are intended to encompass different orientations in addition to the orientation depicted in the figures. For example, if an object in the figures is turned over, elements described as "below" or "beneath" other elements or features would then be oriented "above" the other elements or features. Thus, the exemplary term "below" can, for example, encompass both an orientation of above and below. An object may be otherwise oriented (e.g., rotated 90 degrees or at other orientations) and the spatially relative descriptors used herein may be interpreted accordingly.

Unless clearly indicated to be otherwise only, all connections and all operative connections may be direct or indirect. Similarly, unless clearly indicated to be otherwise only, all connections and all operative connections may be rigid or non-rigid.

Like numbers refer to like elements throughout. Thus, the same or similar numbers may be described with reference to other drawings even if they are neither mentioned nor described in the corresponding drawing. Also, even elements that are not denoted by reference numbers may be described with reference to other drawings.

Many different forms and embodiments are possible without deviating from the spirit and teachings of this disclosure and so this disclosure should not be construed as limited to the example embodiments set forth herein.

With global outbreaks of deadly contagious diseases becoming more regular, frequent glove changes are required in medical industries, food industries, and law enforcement agencies, for example. A practical glove-dispensing machine would save time and help prevent spread of contagious agents.

FIG. 1 is a front view of a conventional flexible glove 20 that may include an upper region 22, a middle region 24, and a lower region 26 of glove material. For convenience, the regions are shown as separated by a virtual distal broken line 14 and a virtual proximal broken line 16. The upper region includes multiple finger sleeves or finger parts 28a, 28b, 28c, and 28d (collectively finger parts 28). In some embodiments, the finger parts 28 may have substantially the same size. However, in many embodiments, the finger part 28d may be the shortest, and/or it may have the smallest circumference or diameter. The finger part 28b may be the longest, and/or it may have the largest circumference or diameter. The finger parts 28a and 28c may have similar lengths, circumferences, and/or diameters, and these finger parts 28a and 28c may be generally smaller than those of the finger part 28b and generally larger than those of the finger part 28d. In some embodiments, the finger part 28c may have slightly larger dimensions than those of the finger part 28a.

The middle region 24 may include a palm part 30 and a back part (not shown) that are configured to cover the palm region of a hand. A thumb part 34 may form part of the middle region 24, the upper region 22, or both the middle region 24 and the upper region 22. The lowest portion of the thumb part 34 may be positioned in the middle region 24 or the upper region 22. The thumb part 34 may have a wider circumference and diameter than those of the finger parts 28, and the thumb part 34 may be shorter than the finger parts 28. However, the thumb part 34 may be longer than or equal to the finger part 28d.

Figure 2:
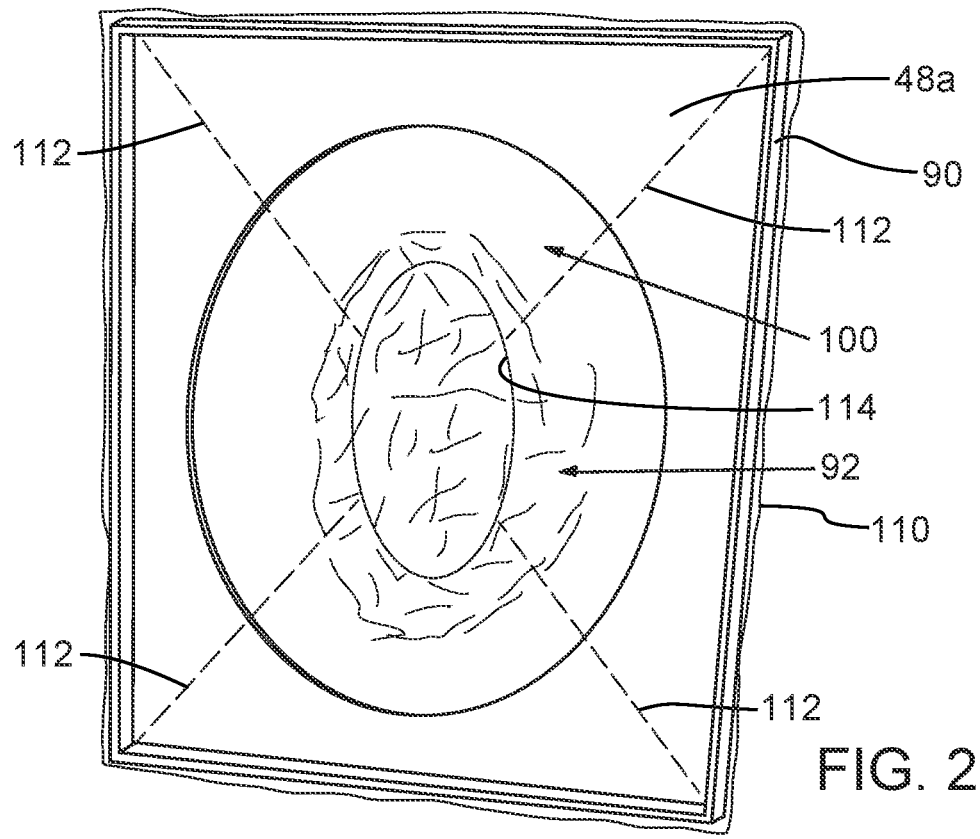
FIG. 2 is a front perspective view of a glove cartridge, including a flexible glove.

The lower region 26 may include a wrist part 36 and a glove base 38 that defines a glove opening 40. In FIG. 2, the glove base 38 and glove opening 40 are depicted in a relaxed, at least partly open, and unstretched condition. The glove base 38 may include a glove lip 42 that includes a thicker region of glove material. The glove lip 42 may extend along the entire perimeter of the glove base 38, or the glove lip 42 may extend only partly around the entire perimeter, such as a major portion of the perimeter or a minor portion of the perimeter. Additionally, the glove lip 42 may be continuous or noncontinuous, and the glove lip 42 may have uniform thickness, or the glove lip 42 may have some regions where the glove lip 42 is thicker than in other regions. The glove 20 may comprise a polymer material. Some glove materials include one or more of a nitrile material, a vinyl material, or a latex material.

The gloves 20 may be configured as a "one size fits all" glove 20, or the gloves 20 may be configured in different sizes, such as: large and small; large, medium, and small; or extra large, large, medium, small, and extra small. The different sizes may include different lengths or circumferences for the finger parts 28, and/or different dimensions for the palm part 30 or the opening 40. The gloves 20 may all have the same color, or different sizes of gloves 20 may be manufactured with different colors so that the different sizes are readily discernable.

The glove opening 40 may be circular, oval, elliptical, or other shape in a relaxed (nonstretched) at least partly open state. Regardless of shape, perimeter and circumference are used interchangeably herein for convenience. In some embodiments, the glove opening 40 for a small glove 20 may have a perimeter of 200 mm plus or minus 5 mm, the glove opening 40 for a medium glove 20 may have a perimeter of 210 mm plus or minus 5 mm, and the glove opening 40 for a large or an extra large glove 20 may have a perimeter of 220 mm plus or minus 5 mm.

The glove base 38 or the glove opening 40 may have a major opening dimension 32 along a major opening axis 44 and a minor opening dimension 46 along a minor opening axis 88. The major opening axis 44 may be generally parallel with a major plane of the middle region 24 or palm part 30. These dimensions will vary depending on whether the glove is in a stretched state or a relaxed state. In a relaxed state, the major opening axis 44 may be an inverse function of the minor opening dimension 46 and vice versa. However, these axes and dimensions may be useful for describing orientation.

FIG. 2 is a front perspective view of a glove cartridge 50, including the flexible glove 20; and, FIGS. 3-6 are respective front, side, top, and perspective views of a cartridge 52 without the glove 20. The glove cartridge 50 may also be referred to as a glove cartridge assembly because it includes a glove 20 that is reversibly attached to a cartridge 52. With reference to FIGS. 2-6, the cartridge 52 may include a cartridge frame 54 having a cartridge frame boundary (or cartridge frame outer perimeter) 56 and a cartridge aperture 58 having an aperture inner edge (or cartridge frame inner perimeter) 60. A major surface 48 of the cartridge 50 may extend from the cartridge frame boundary 56 to the cartridge aperture 58.

The cartridge frame boundary 56 may have any shape, such as elliptical, oval, circular, or polygonal. Possible polygonal shapes for the cartridge frame boundary 56 may include, but are not limited to, rectangular, square, pentagonal, hexagonal, octagonal, or dodecagonal. The polygon may include one side or pair of sides that are dissimilar from other sides in shape or length so as to facilitate handling of the glove cartridge 50 in a dedicated orientation. For example, the cartridge frame boundary 56 may have a top side 72 that has a top dimension 74 that is greater than or equal to a side dimension of a left or right side 78. One will appreciate that the shape of the cartridge frame boundary 56 (and/or the dimensions of its sides) may be useful for error-proofing that the cartridges 52 are oriented correctly when placed into holding chambers 122 (FIG. 7), as later described. One will appreciate, alternatively, that all sides or opposite sides may have equal length dimensions.

Similarly, the aperture inner edge 60 may have any shape, such as elliptical, oval, circular, or polygonal. Possible polygonal shapes for the aperture inner edge 60 may include, but are not limited to, rectangular, square, pentagonal, hexagonal, octagonal, or dodecagonal. The aperture 58 may have a major aperture dimension 80 along a major aperture axis 82 that propagates through the central axis 70, and the aperture 58 may have a minor aperture dimension 84 along a minor aperture axis 86 that propagates through the central axis 70. The major aperture axis 82 and the minor aperture axis 86 are typically transverse and may be perpendicular. The major aperture axis 82 may bisect the top side 72 and the bottom side, and the minor aperture axis 86 may bisect the left and right sides 78. However, alternative major aperture axes 82 may run through opposite corners.

In some embodiments, a small cartridge aperture 58 may have a perimeter that is 38% plus or minus 5% larger than a small glove opening 40. In one example, a small cartridge aperture 58 may have a perimeter that is 277 mm plus or minus 14 mm. In some embodiments, a medium cartridge aperture 58 may have a perimeter that is 39% plus or minus 5% larger than a medium glove opening 40. In one example, a medium cartridge aperture 58 may have a perimeter that is 294 mm plus or minus 15 mm. In some embodiments, a large or extra large cartridge aperture 58 may have a perimeter that is 50% plus or minus 5% larger than a large or extra large glove opening 40. In one example, a large or extra large cartridge aperture 58 may have a perimeter that is 331 mm plus or minus 16.5 mm.

The aperture dimensions may be based on the glove size and glove material and may also be brand dependent. In some embodiments, the major aperture dimension 80 may be approximately 40-50% larger than the glove opening 40. A determinate factor for aperture size may be elasticity of the glove 20 being mounted to the cartridge 52. The aperture dimensions may be tuned to fit a certain brand of the glove 20 in a manner that permits the glove base 38 or glove lip 42 to be mounted without over-stretching it, while the glove base 38 or glove lip 42 provides sufficient elastic force to stay on the cartridge 52 until the hand 190 (FIG. 18B) is inserted and pressure is applied to force removal of the glove 20 from the cartridge 52. Similarly, the degree of stretch of the glove opening 40 may be based upon a use case for each glove to cartridge mating system. For example, the glove base 38 may be stretched to a large degree in the case of a nitrile glove, but a smaller or even no degree in the case of vinyl or other types of gloves 22.

In some embodiments, the cartridges 52 may all have the same shape and size for the cartridge frame boundary 56 regardless of whether the cartridges 52 support different sizes of gloves 20. In such embodiments, the cartridge apertures 58 may have different sizes or shapes to accommodate the potentially different sizes of the perimeters of the glove bases 38, if useful. The cartridge apertures 58 of different sizes may provide a useful visual cue for distinguishing the different sizes of gloves 20 carried by the cartridges 52. One will appreciate, however, that the cartridges 58 supporting different sizes of gloves 20 may have cartridge apertures 58 of identical sizes and shapes as well as frame boundaries 56 of identical sizes and shapes. The flexibility or stretchability of the glove material may permit such uniformity of the cartridges 52.

In some of such embodiments, the cartridges 52 may have different signature colors for each glove size and/or the gloves 20 may have different signature colors for each glove size, as previously mentioned, as a useful visual cue for distinguishing the different sizes of gloves 20 carried by the cartridges 52. The signature coloring may cover all or parts of the cartridge 50, such as one or both major surfaces 48 (front major surface 48a and back major surface 48b) of the cartridge 50.

Alternatively, the cartridges 52 may have a different shape and/or size for the cartridge frame boundary 56 for different sizes of gloves 20. For example, the cartridges 52 may be configured with decreasing sizes to coordinate with decreasing sizes of gloves 20. Alternatively or additionally, the frame boundaries 56 of the cartridges 52 may be configured with different numbers of sides to coordinate with the sizes of gloves. For example, a cartridge 52 for a large glove 20 may be configured with eight sides; a cartridge 52 for a medium glove 20 may be configured with six sides; and a cartridge 52 for a small glove 20 may be configured with four sides.

In some embodiments, the cartridge 52 has a major axis (along a side or along a diagonal) that is less than or equal to 155 mm (6 inches). In some examples of rectangular frame boundaries 56, the frame boundary dimensions are 101.6 mm plus or minus 25 mm by 127 mm plus or minus 25 mm. In some examples of rectangular frame boundaries, at least two of the frame boundary dimensions differ by greater than 10 mm, 15 mm, or 25 mm. Cartridges 52 with different shapes or with different dimensions along different sides may be useful to ensure placement of respective different cartridges 52 into respective holding chambers 122 and/or may be useful to ensure that the cartridges 52 are placed into the holding chambers 122 in a desirable orientation.

With or without different cartridge configurations, the cartridges 52 may be color coded to reflect different glove sizes. One will appreciate, however, that having uniform sizes or similar shapes (such as rectangles of the same or different sizes) for cartridge frame boundaries 56 regardless of different glove sizes may simplify considerations for a glove-dispensing machine, as later described. The cartridges 52 may also include alternative keying features, such as one or more notches or outward tabs along one or more of the sides of the frame boundaries 56 that are matched to particular holding chambers 122 and/or particular orientations within the holding chambers 122, to facilitate placement of specific cartridge types into specific holding chambers 122 in specific orientations. Moreover, cartridges 52, especially cartridges 52 having identical frame boundary dimensions but supporting different-sized gloves 20, may be equipped with machine-identifiable size information. Machine sensors may be employed to identify size or other information by cartridge color or by sensing RFID tags that contain desirable information such as size.

An aperture ridge 62 may be in proximity to the aperture inner edge 60 and may extend along at least a portion of the aperture edge 60. Proximity to aperture inner edge 60 may be less than or equal to 1 cm, less than or equal to 0.5 cm, or less than or equal to 0.25 cm, or may be at the aperture inner edge 60, itself. In FIGS. 2-6, the aperture ridge 62 is shown protruding from the front major surface 48*a*. One will appreciate, however, that the aperture ridge 62 may protrude from the back major surface 48*b*. In other embodiments, both the front major surface 48*a* and the back major surface 48*b* may each support an aperture ridge 62. (In some embodiments, both the front and back sides of the cartridge 50 may be identical, which may be advantageous for manufacture or manipulation.)

The aperture ridge 62 may extend along the entire perimeter of the aperture edge 60. However, the aperture ridge 62 may extend along only a major portion of the aperture edge 60 (i.e., greater than or equal to half the perimeter of the aperture edge 60), or the aperture ridge 62 may extend along a minor portion of the aperture edge 60 (i.e., less than or equal to half the perimeter of the aperture edge 60). The aperture ridge 62 may be a continuous structure, or it may be a discontinuous structure, including one or more breaks along the aperture edge 60, forming multiple aperture tabs 62*a*. Moreover, the aperture ridge 62 may have a uniform cross-sectional profile along its length, or the aperture ridge 62 may have a nonuniform cross-sectional profile along its length, with regions having different cross-sectional profiles or sizes. A discontinuous aperture ridge 62 (aperture tabs 62*a*) may permit less force to be applied to disconnect a glove 20, facilitating easier glove removal by an inserted hand 190. Accordingly, the amount of the aperture ridge 62 along the aperture edge 60 may be configured to the specific size, elasticity, and/or brand of the glove 20.

The aperture ridge 62 may have a ridge base 64 and an optional ridge lip 66, wherein the aperture inner edge 60 is closer to the ridge base 64 than to the ridge lip 66. The ridge base 64 may have a base perimeter that is smaller than a lip perimeter of the ridge lip 66, potentially forming a recess 68 between the ridge lip 66 and a major surface 48 of the cartridge 52. For example, the aperture ridge 62 may flare outwardly (with respect to a central axis 70 of the cartridge aperture 58) from the ridge base 64 to the ridge lip 66. In another example, the ridge base 64 may extend generally perpendicularly from the plane of the cartridge aperture 58, and the ridge lip 66 may extend outwardly (with respect to the central axis 70 of the cartridge aperture 58) from the ridge base 64. The ridge lip 66 may be transverse to the ridge base 64, extending toward or away from the plane of the aperture 58 or generally perpendicular to the plane of the aperture 58.

The aperture ridge 62 could alternatively flare inwardly. A perpendicular or inward flare would decrease complexity in a cartridge injection mold design, as such ridges 62 would allow the use of a simple two-piece mold. An outward flare might utilize additional mold slides to form the underlying recess. However, cartridges may be manufactured by on-demand printing that could readily accommodate any design features.

The ridge base 64 or ridge lip 66 may be continuous structures, or they may be discontinuous structures, including one or more breaks along the aperture edge 60. One will appreciate that their continuities need not be the same. Moreover, they may have uniform cross-sectional profiles along their lengths, or they may have nonuniform cross-sectional profiles along their lengths, with regions having different cross-sectional profiles or sizes. The dimensions of the ridge base 64 or ridge lip 66 may be configured to the specific size, elasticity, brand of the glove 20, and/or the amount of the aperture ridge 62 along the aperture edge 60.

The major cartridge surface 48 may have surface area that includes all of the area between the cartridge frame boundary 56 and the cartridge aperture 58. Alternatively, the major cartridge surface 48 may be skeletal in nature having sufficient struts or other connections between the cartridge frame boundary 56 and the cartridge aperture 58 to sustain structural integrity. The cartridge surface 48, itself, may be flat or textured. There may, however, be air-pressure-containment advantages or hygienic or sterilization advantages for having a flat, uniform, continuous surface between the cartridge frame boundary 56 and the cartridge aperture 58. The cartridge surface 48 may employ a transparent, semi-transparent, or translucent material, or may include one or more windows of such materials. Even so, color coding of the cartridges would still be possible.

In some embodiments, the major cartridge surface 48 exhibits no slope from the cartridge frame boundary 56 to the cartridge aperture 58, such that the cartridge frame boundary 56 and the cartridge aperture 58 lie in the same plane. In some embodiments, the major cartridge surface 48 slopes from the cartridge frame boundary 56 to the cartridge aperture 58 so that the cartridge frame boundary 56 and the cartridge aperture 58 lie in different planes. The slope can be forwardly or backwardly with respect to the front cartridge surface 48*a*. A sloped surface 48 may be advantageous for providing space for the glove 20 when it is in a collapsed configuration 92, which is shown in FIG. 2.

The cartridge 52, at or near the cartridge frame boundary 56, may have a boundary wall 90 (FIG. 2) that is transverse to the major cartridge surface 48. The boundary wall 90 may taper outwardly (with respect to the cartridge aperture 58) from its boundary wall base at the major cartridge surface 48 to its boundary wall top. The boundary wall 90 could instead be perpendicular to the major cartridge surface 48, or the boundary wall 90 could taper inwardly.

One will appreciate that an outward flare may facilitate stacking the cartridges on top of each other with their surface planes being substantially parallel. The outward taper of the boundary wall 90 may extend from the front cartridge surface 48*a* as shown in FIG. 2, or it may extend from the rear cartridge surface 48*b*. In some embodiments, the boundary wall 90 may extend from both major cartridge surfaces 48, with an outward taper on one side and an inward taper on the other side to improve seating of the cartridges 52 while in a stack. For example, the front surface 48*a* with a boundary wall 90 with an outward taper may be configured to provide a receptacle for the rear surface 48*b* of another glove cartridge 50 with or without a boundary wall 90 with an inward taper on its rear surface 48*b*.

However, many embodiments that do include a boundary wall 90 have it only on one side of the cartridge 52 so that the cartridge 52 can present a flat surface to a back surface 176 of a glove portal face 178, as later described with respect to FIG. 16A. One will appreciate that the height(s) and flare(s) of aperture ridge 62 and the boundary wall 90 may be configured to permit sliding of one cartridge 52 across another cartridge 52 in response to an intentionally applied force greater than a predetermined amount, such as to move a selected cartridge 52 from a holding chamber 122, as later described. One will also appreciate that it is possible to have boundary walls 90 on fewer than all sides of the cartridge frame 54. For example, putting boundary walls 90 on only two parallel frame sides (such as the longer frame sides) may allow the cartridges 52 to stack together, while allowing stacked cartridges to substantially easily slide relative to each other in one or both directions along an axis that is parallel to the parallel sides. This embodiment would facilitate automated conveyance of a glove cartridge 50 from the holding chamber 122, such as employing a cartridge deck actuator 152 (FIG. 15) to push a cartridge 52 from the bottom or top of a stack.

The glove 20 may be seated on the cartridge 52 in a number of ways. The glove base 38, with or without, a glove lip 42 may be positioned around the aperture ridge 62. In particular, the glove base 38 or glove lip 42 may be positioned at the ridge base 64, or between the ridge base 64 and the ridge lip 66, such that the glove base 38 and the glove opening 40 are positioned about the cartridge aperture 58 in a stretched condition 100 with the interior of the glove 20 facing frontwards with respect to the front major surface 48*a* of the cartridge 52 (regardless of whether the aperture ridge is positioned on the front major surface 48*a* or on the rear major surface 48*b*).

The glove 20 may be oriented to the cartridge 52 so that its major opening axis 44 is generally collinear with, or generally parallel with the major aperture axis 82 of the cartridge 52. For example, the major opening axis 44 of the glove 20 may be generally collinear or generally parallel with a major aperture axis 82 that bisects the top side 72 and bottom side of the cartridge 52, or the major opening axis 44 of the glove 20 may be generally collinear or generally parallel with a major aperture axis 82 that runs through the corners of the cartridge 52. One will, however, appreciate that the major opening axis 44 may be positioned with other orientations with respect to the cartridge 52. For example, the major opening axis 44 may be oriented at a glove-orientation angle with respect to the major aperture axis 82 that bisects the top side 72 and bottom side of the cartridge 52. However, the glove-orientation angle may be less than or equal to 45 degrees, less than or equal to 30 degrees, less than or equal to 25 degrees, less than or equal to 15 degrees, less than or equal to 10 degrees, or less than or equal to 5 degrees.

In some embodiments, one or both faces of the glove cartridge 50 may be hermetically sealed or partly sealed such as by a wrap or film 110. The film 110 may help maintain the glove 20 in the collapsed configuration 92 during transport, storage, and manipulation of the glove cartridge 50. The film 110 may be a plastic or other layer material and may be configured with indentations or perforations along predetermined tear lines 112. In one embodiment shown in FIG. 2, the film 110 covers a stretched portion of the lower region 26 of the glove 20 so that the interior opening of the finger parts 28 are accessible through an opening (or film aperture) 114 in the film 110. In FIG. 2, the tears lines 112 are generally aligned with the major aperture axes 82 and extend from the corners of the cartridge 52 to the film opening 114. The film opening 114 may have a border that is continuous as shown in FIG. 2, or the border may include tear lines such as any type of perforation.

Figure 2A:
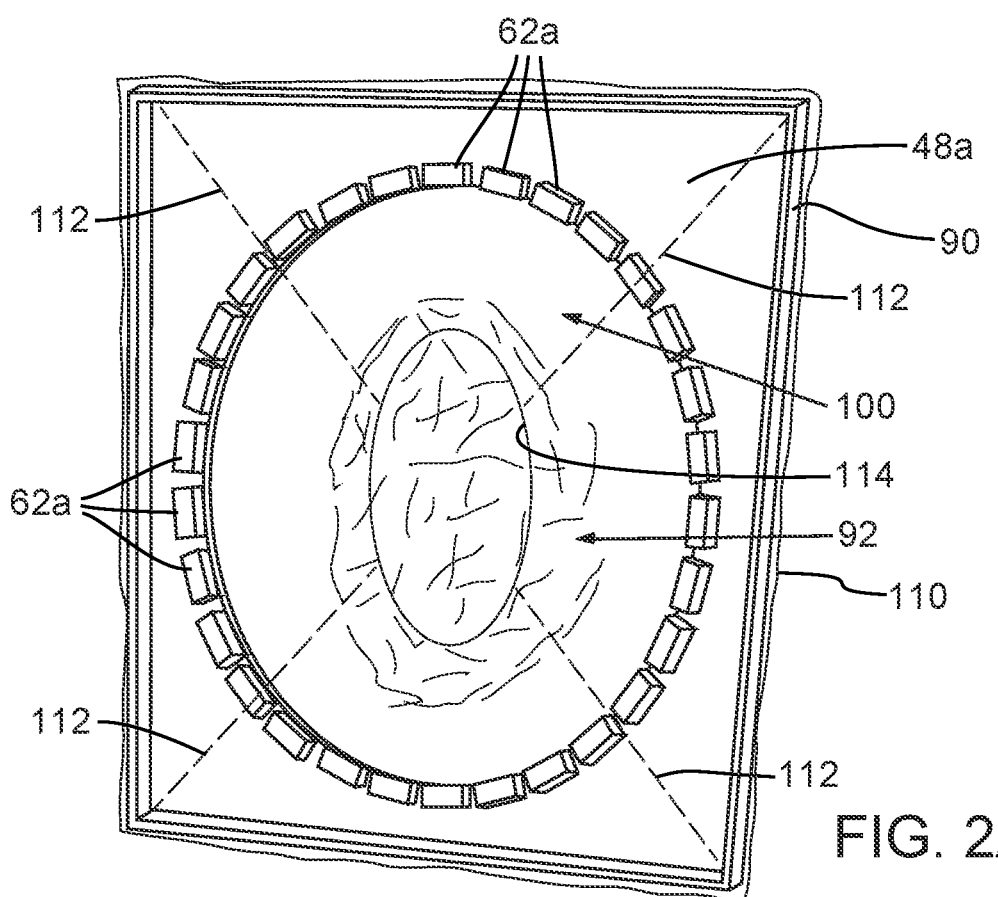
FIG. 2A is a front perspective view of an alternative glove cartridge, including a flexible glove.
Figure 6:
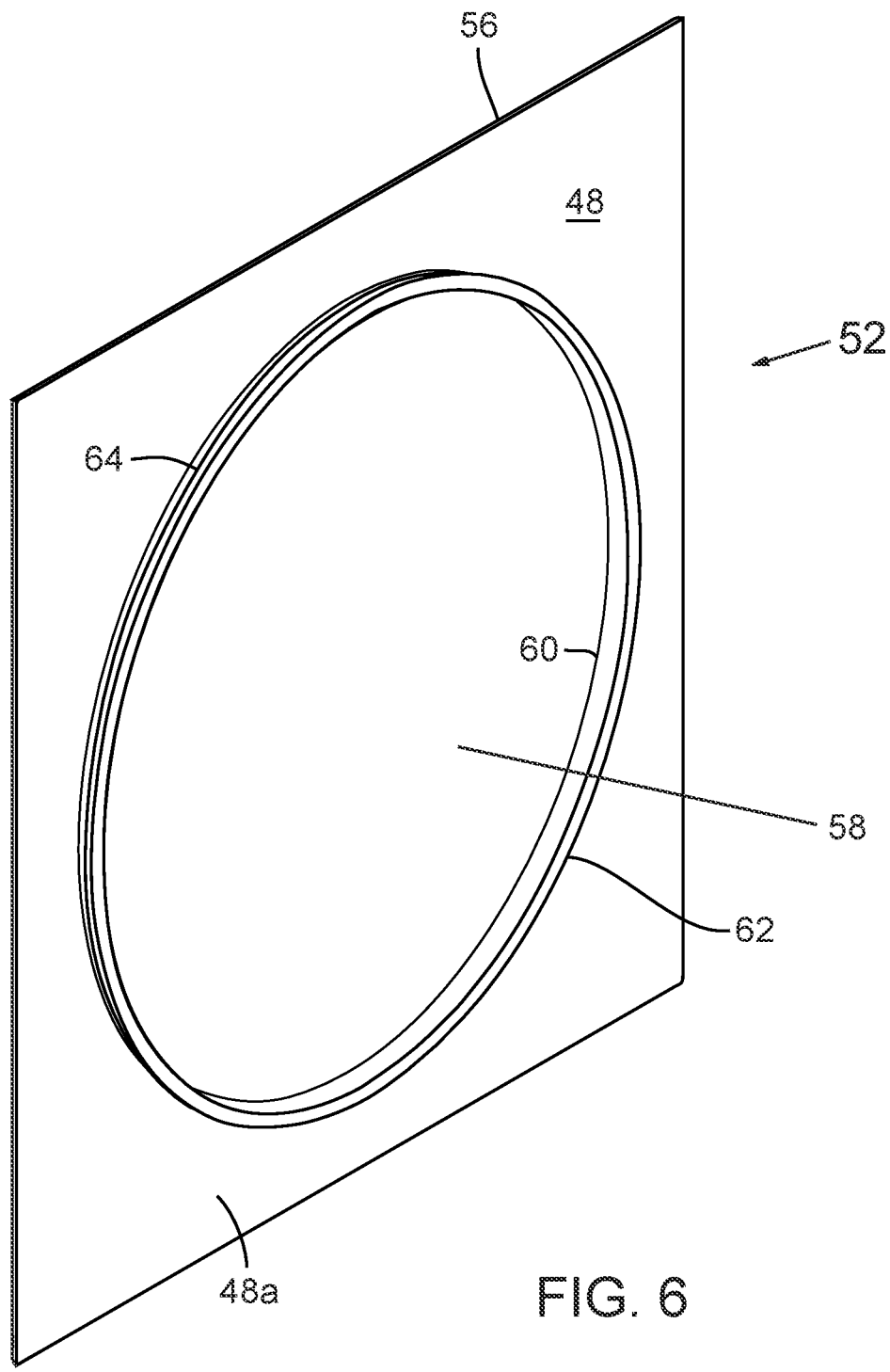
FIG. 6 is a front and left side perspective view of the cartridge.

Film 110 may be transparent as shown in FIGS. 2 and 2A; however, it may be opaque, have color, and/or have size information, logos, and/or advertising. In some embodiments, glove cartridges 50 having gloves 20 of different sizes may have different colors or patterns so that they can be readily distinguished from each other. One will appreciate that the film 110 may completely cover one or both faces of the glove cartridge 50 and use any type of tear lines or perforations to create a tear-through film opening 114 instead of a pre-existing film opening 114.

In some embodiments, the glove cartridge 50 may include an additional cartridge aperture 58 that may have any of features previously discussed and that may support an additional flexible glove 20 having any of features previously discussed. In such embodiments, the major cartridge surface 48 may be substantially planar, or it may be angled between the two glove apertures 58. The angle between the planes may be between two axes or between three axes.

FIG. 7 shows a portion of a glove-dispensing machine 120 having multiple holding chambers 122*a*, 122*b*, and 122*c* (collectively holding chambers 122) for holding stacks of glove cartridges 50, with each stack having different sizes of gloves 20. Generally, certain dimensions, such as the length and/or width dimensions, for each holding chamber 122 will be same, especially if all of the cartridges 52 have frame boundaries 56 with the same sizes and shapes. These holding chambers may have some dimensions that are slightly greater than the dimensions of the frame boundary 56 to facilitate stacking of the glove cartridges 50. Some of the holding chambers 122 may have one dimension, such as height, that may differ among the holding chambers 122 to accommodate more or less numbers of glove cartridges 50 that may correspond to demographics of hand sizes in general, at a geographic area, or a particular group of employees, for example. One will appreciate that the holding chambers 122 may be divided by moveable shelves so that the holding chambers 122 can be adjusted to accommodate different numbers of cartridges 52 having different glove sizes. One will appreciate however, as noted previously, the cartridges 52 holding the different size gloves 20 may have different sizes or shapes, so the holding chambers 122 may have different sizes or shapes, such as different length and/or width dimensions.

The holding chambers 122 may have chamber doors 124 (with or without handles 108) that swing outwardly from holding chamber side walls 116 on one or more pivot points such as hinges 118. One will appreciate that other door configurations are possible, such as doors 124 that open upwardly to bias a closed-door position. Alternatively, hinges 118 can be biased to close a horizontal swing, for example. In some embodiments, the doors 124 may be configured to slide horizontally to avoid possible contamination caused by air being swept toward the chamber 122 when the door 124 is swinging closed. In other additional or alternative embodiments, the chambers 122 can be supplied with positive air pressure to prevent or inhibit external air from entering the chambers 124.

Figure 23:
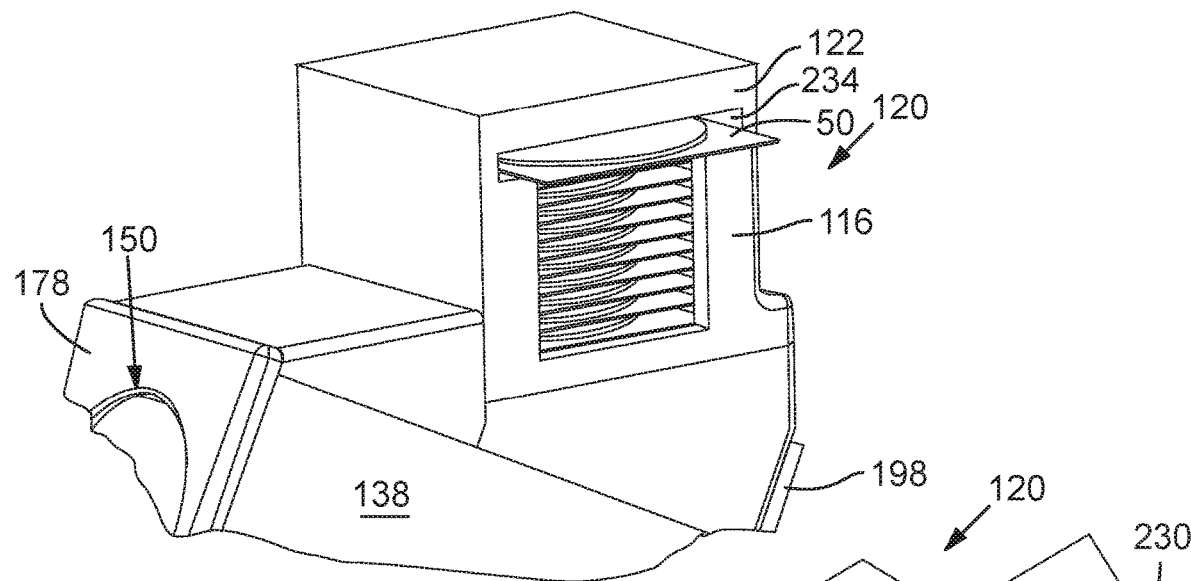
FIG. 23 is a front right isometric view of a portion of an example glove-dispensing machine having a slot-insertion storage chamber that may be employed with or without a door.

Some embodiments of the glove-dispensing machine 120 may omit chamber doors 124. As shown in FIG. 23, the holding chambers 122 instead may have a cartridge-insertion slot 234 in the holding chamber side wall 116 through which the glove cartridges 50 can be manually loaded into the holding chamber 122.

The doors 124 may be marked to indicate a specific glove size to facilitate the loading of the correct glove cartridges into the correct chambers 122. These indicators may include words, initials, and/or colors that designate specific sizes. The holding chambers 122 may be associated with or correspond to size selector mechanisms 126 on a size selector panel 128. For example, the holding chambers 122a, 122b, and 122c may correspond to size selector mechanisms 126c, 126b, and 126a, respectively. The size selector mechanisms 126 may include, push buttons, (re-settable) switches, pull knobs, or other equivalents.

Figure 9:
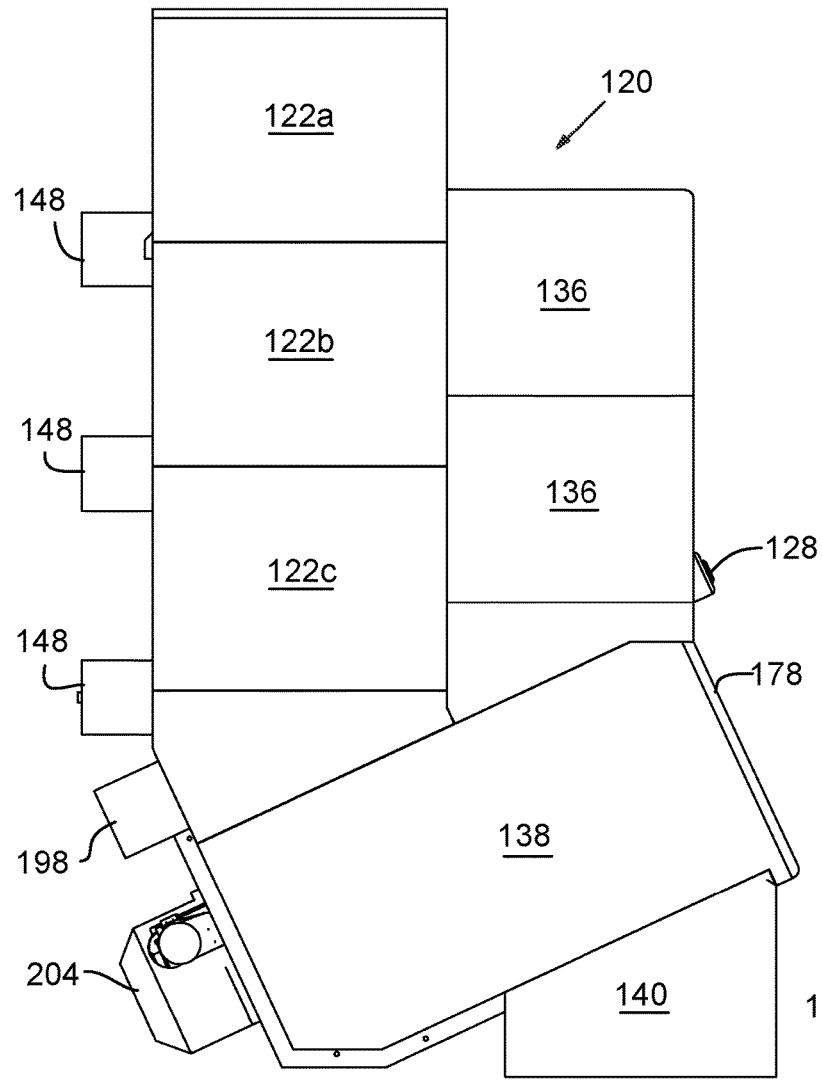
FIG. 9 is a side view of a glove-dispensing machine.
Figure 9A:
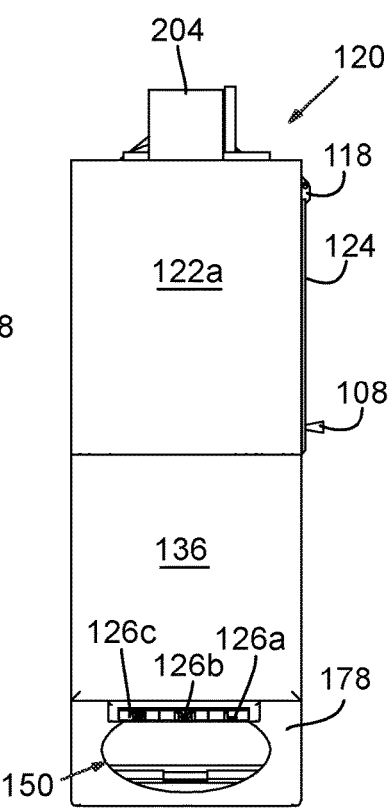
FIG. 9A is a top view of a glove-dispensing machine.
Figure 10:
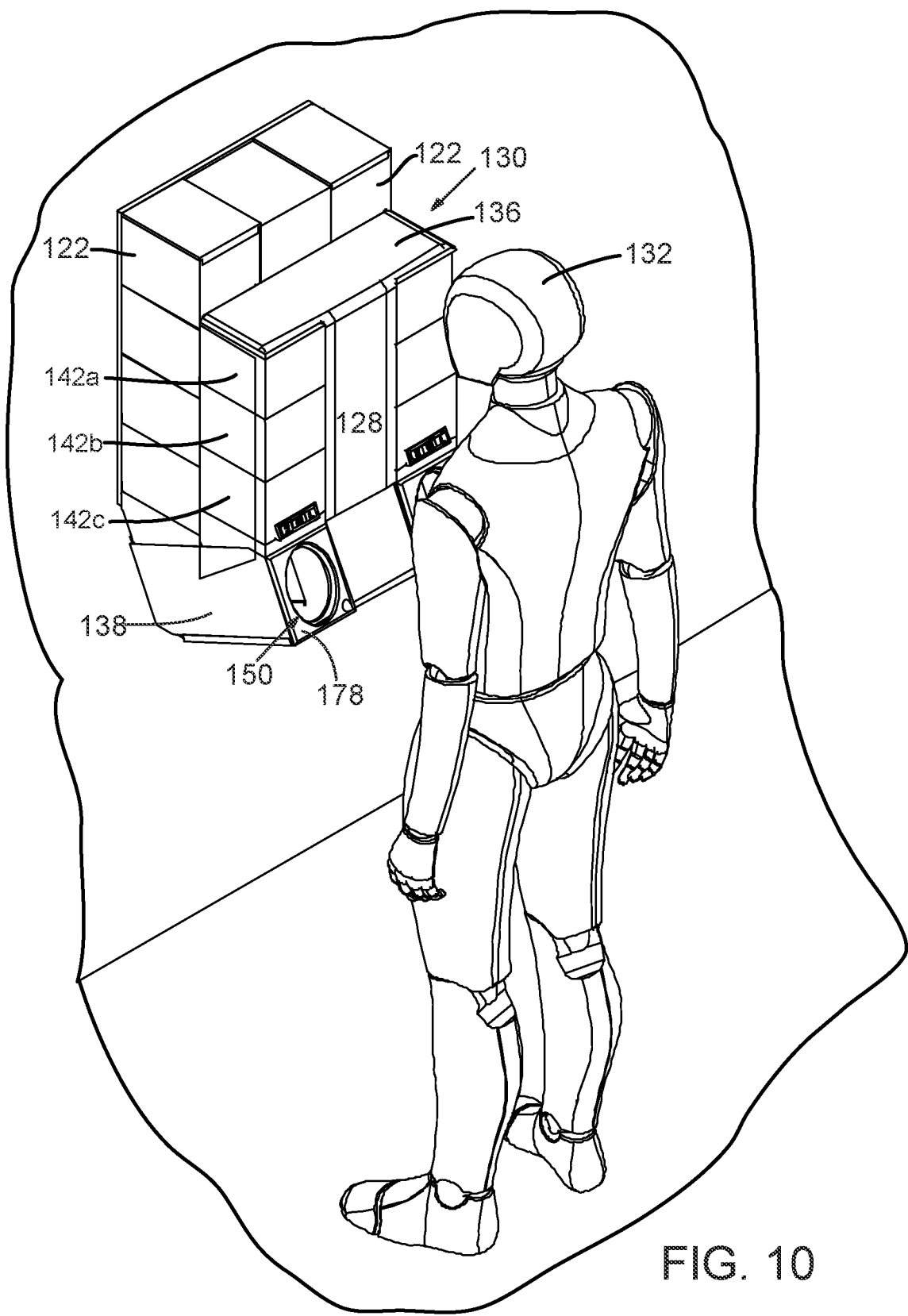
FIG. 10 is a left side and front perspective view of a glove-dispensing system that includes two glove-dispensing machines and a mannequin positioned in front of the system.
Figure 11:
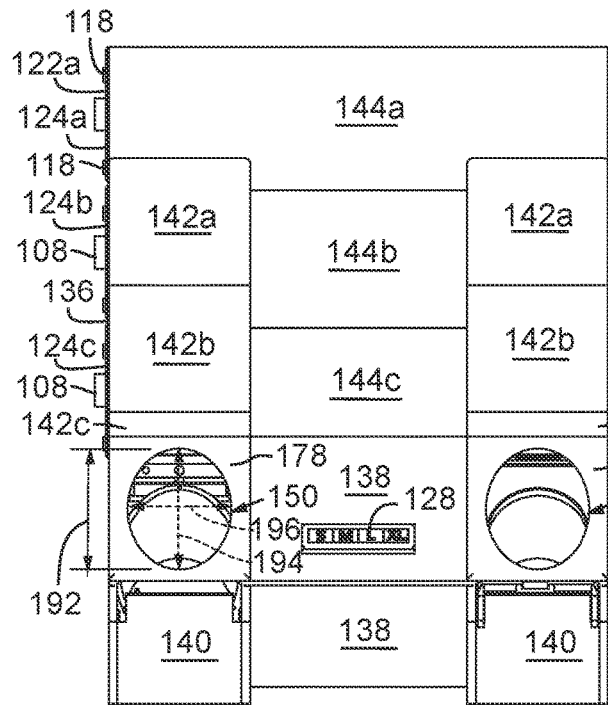
FIG. 11 is a front view of a glove-dispensing system.
Figure 12:
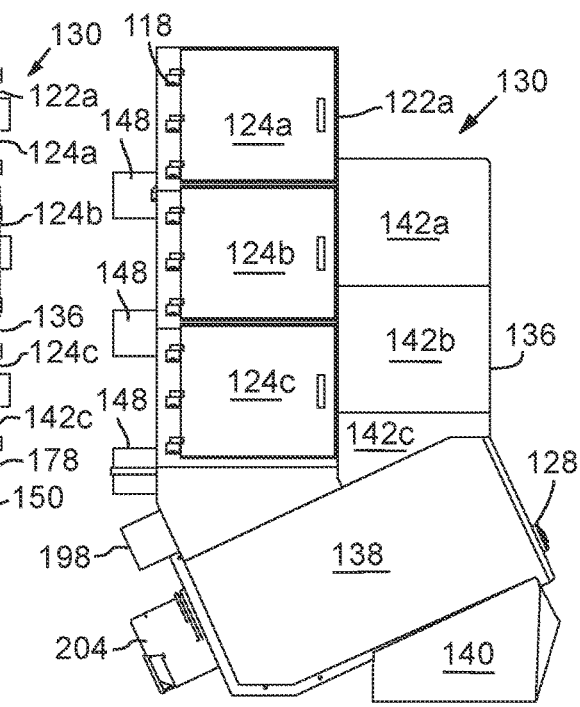
FIG. 12 is a left side view of a glove-dispensing system.
Figure 13:
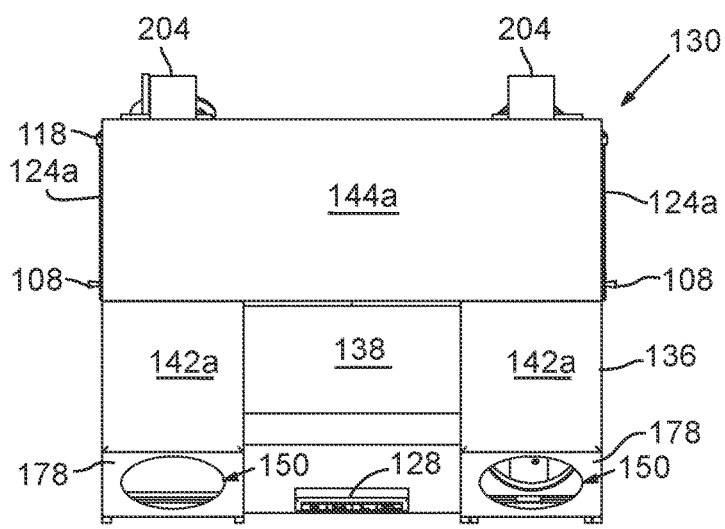
FIG. 13 is a top view of a glove-dispensing system.
Figure 14:
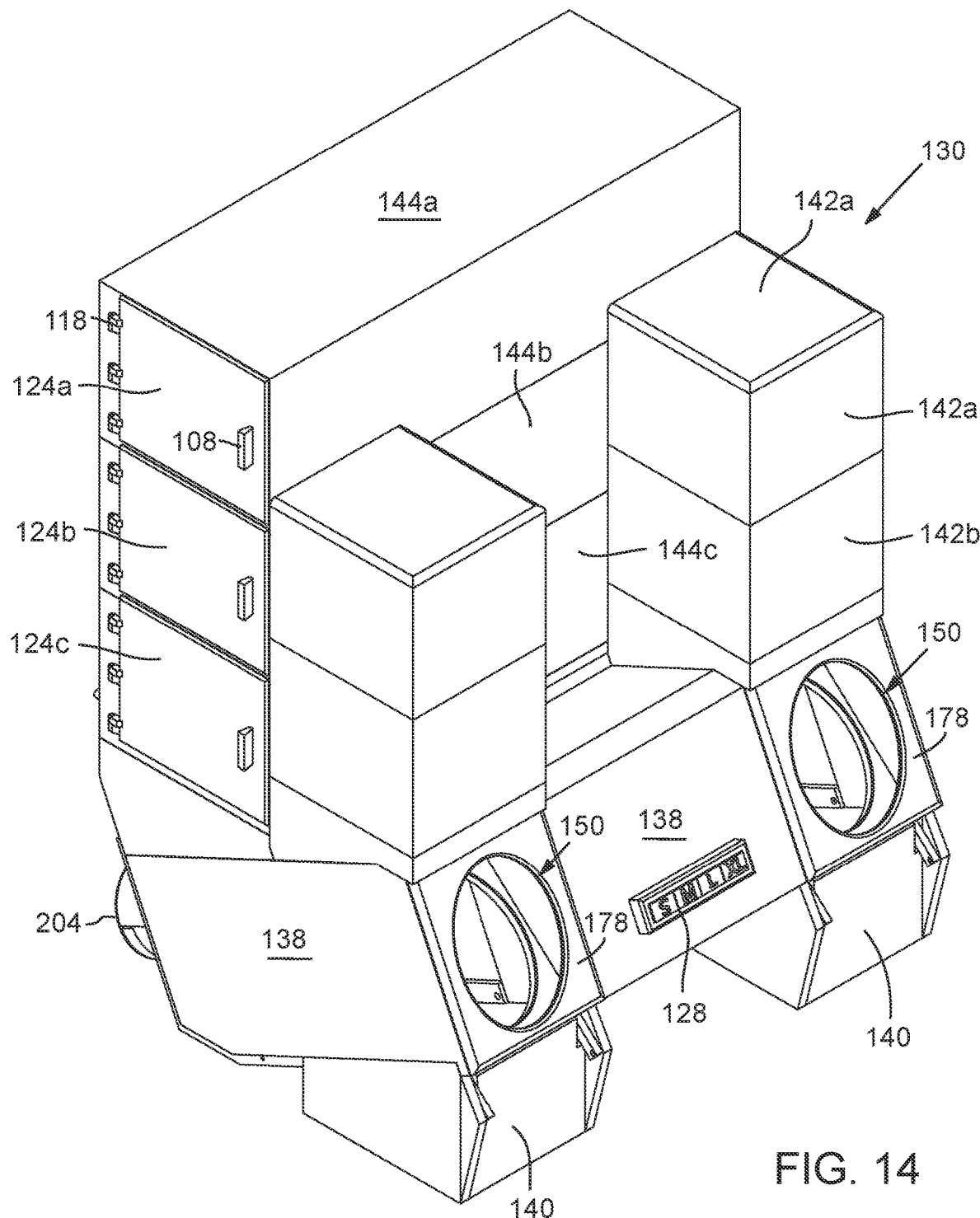
FIG. 14 is a top, left, and front isometric view of a glove-dispensing system.

FIG. 8 is front view of a glove-dispensing machine 120, FIG. 9 is a left side view of the glove-dispensing machine 120, and FIG. 9A is a top view of the glove-dispensing machine 120. FIG. 10 is a left side and front perspective view of a glove-dispensing system 130 that includes two glove-dispensing machines 120 built into a wall 134 with a mannequin 132 positioned in front of the system 130. FIG. 11 is a front view of the glove-dispensing system 130, FIG. 12 is a left side view of the glove-dispensing system 130, FIG. 13 is a top view of the glove-dispensing system 130, and FIG. 14 is a top, left, and front isometric view of the glove-dispensing system 130.

With reference to FIGS. 8-14, the glove-dispensing machine 120 may include a housing upper portion 136, a housing lower portion 138, a base 140, and chamber housings, 144a, 144b, and 144c. The housing upper portion 136 may be positioned in front of the holding chambers 122 and may have multiple separate housing sections or panels 142a, 142b, and 142c. The housing panels 142a, 142b, and 142c (collectively, housing panels 142) may enclose cartridge pathway chambers 146 (FIG. 15), as later described. A glove-dispensing system 130 may include only a single glove-dispensing machine 120 having only a single glove portal 150, such that a user would insert only one hand at a time to receive a glove 20.

However, the glove-dispensing system 130 may include two glove-dispensing machines 120 that are mirror images of each other. However, in some embodiments, some of the components and mechanisms may be mirror images and other components and mechanisms that need not be oriented to a particular side can be substantially similar or substantially identical. One will also appreciate that any portion of the description concerning the glove-dispensing system 130 may also apply to the glove-dispensing machine 120, except where such descriptions can pertain only to a glove-dispensing system 130 that includes two or more glove-dispensing machines 120.

The glove-dispensing system 130 may also include a central spacer portion whose purpose is to space apart the two glove-dispensing machines 120 by a suitable distance to allow a user to don a glove 20 on each hand substantially simultaneously. In some embodiments, the glove-dispensing system 130 may include two size selector panels 128, one for each glove-dispensing machine 120 to accommodate people who have hands of different sizes. However, the glove-dispensing system 130 may include only a single size selector panel 128 to provide gloves 20 of the same size at each glove portal 150. Moreover, for a two-hand glove-dispensing system 130, a number of components may be centralized, such as a main controller and/or a vacuum pump, for example, as later described. Also, the space between the mirrored machines 120 (or partly mirrored machines 120) may be used to house components, allowing the over system size to be smaller.

Figure 15:
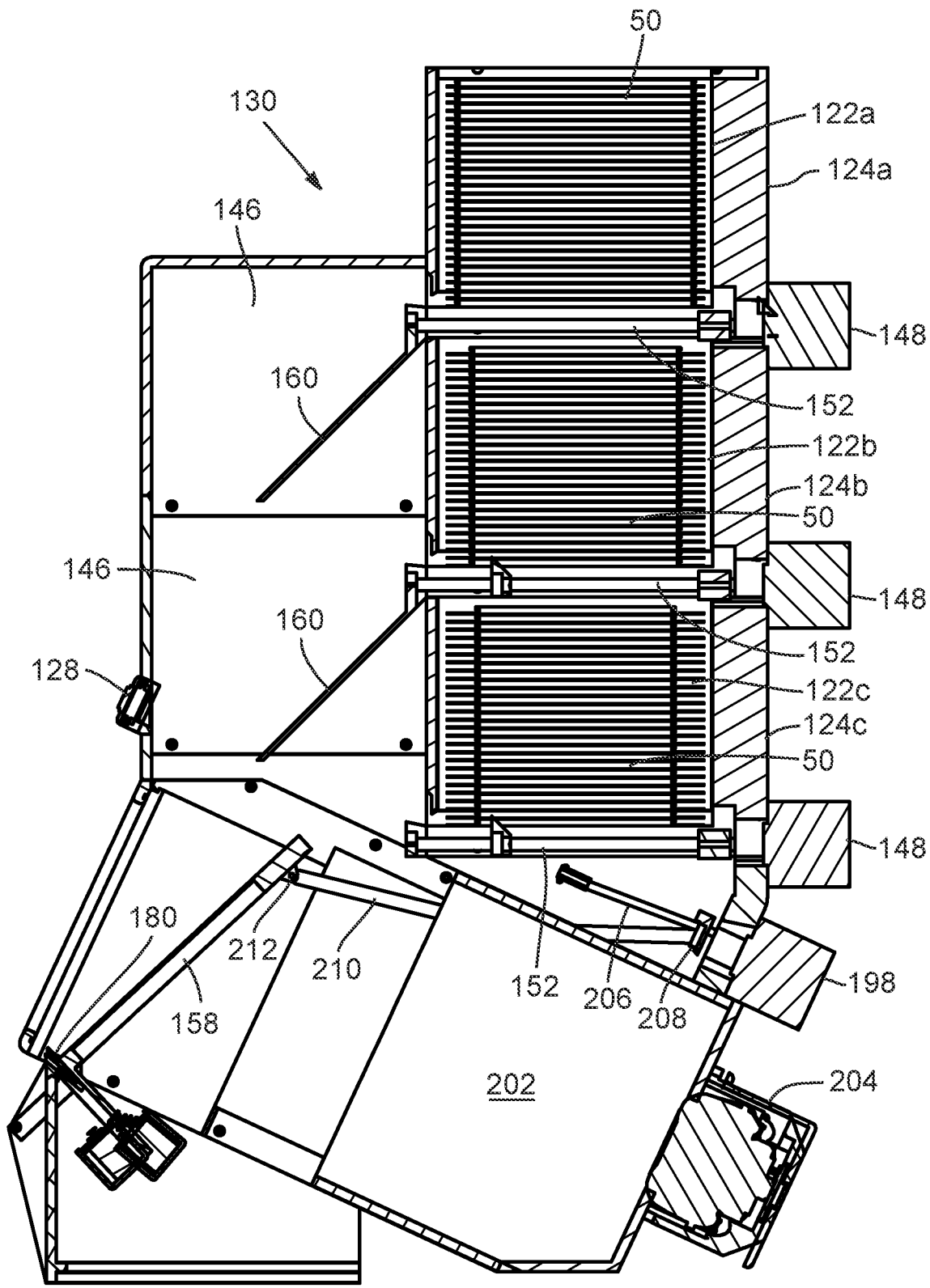
FIG. 15 is a right side cross-sectional view of a glove-dispensing system showing internal components.
Figure 16A:
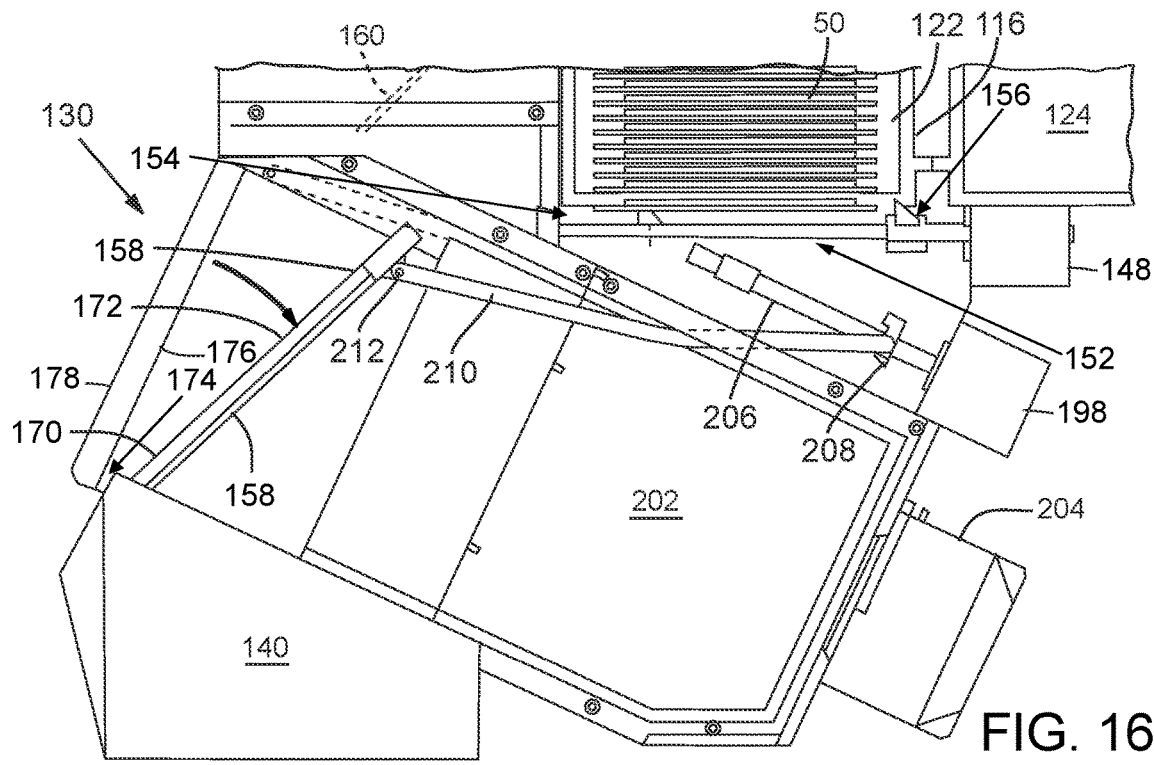
FIGS. 16A, 16B, 16C, and 16D are right side cross-sectional views of a glove-dispensing region of a glove-dispensing system, showing an example of a portion of a sequence for loading a cartridge into a glove-dispensing position.
Figure 16B:
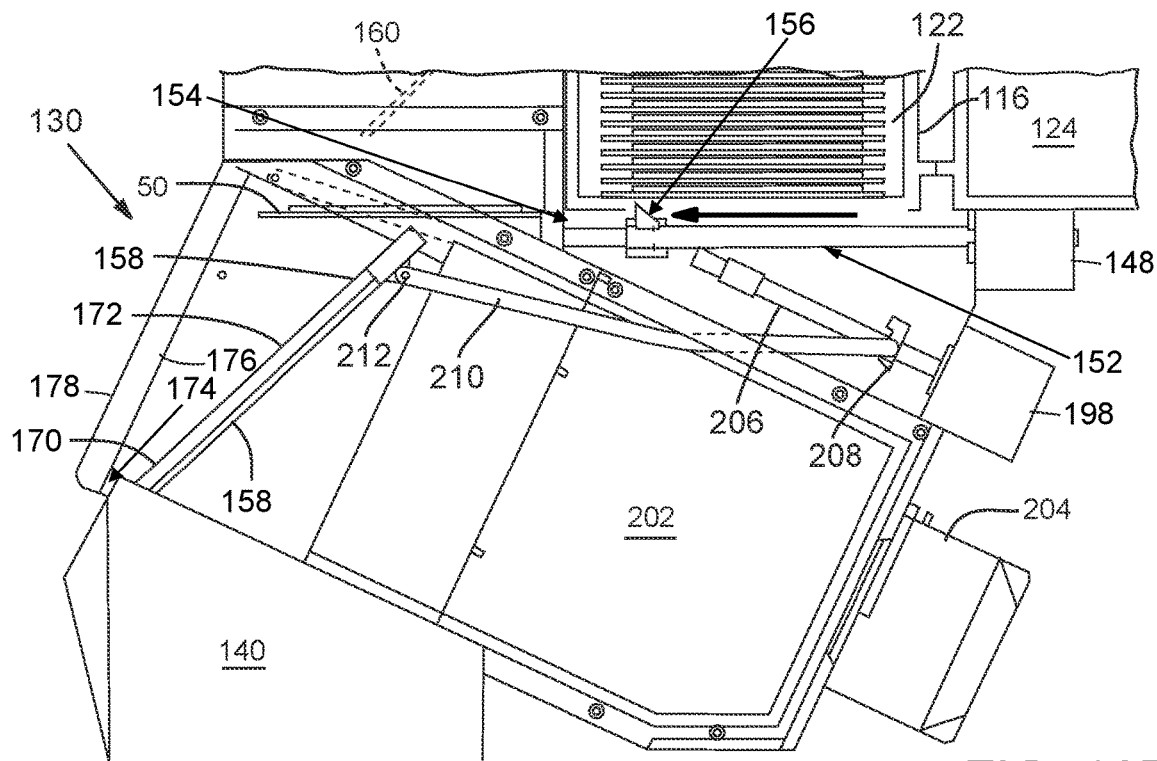
Figure 16C:
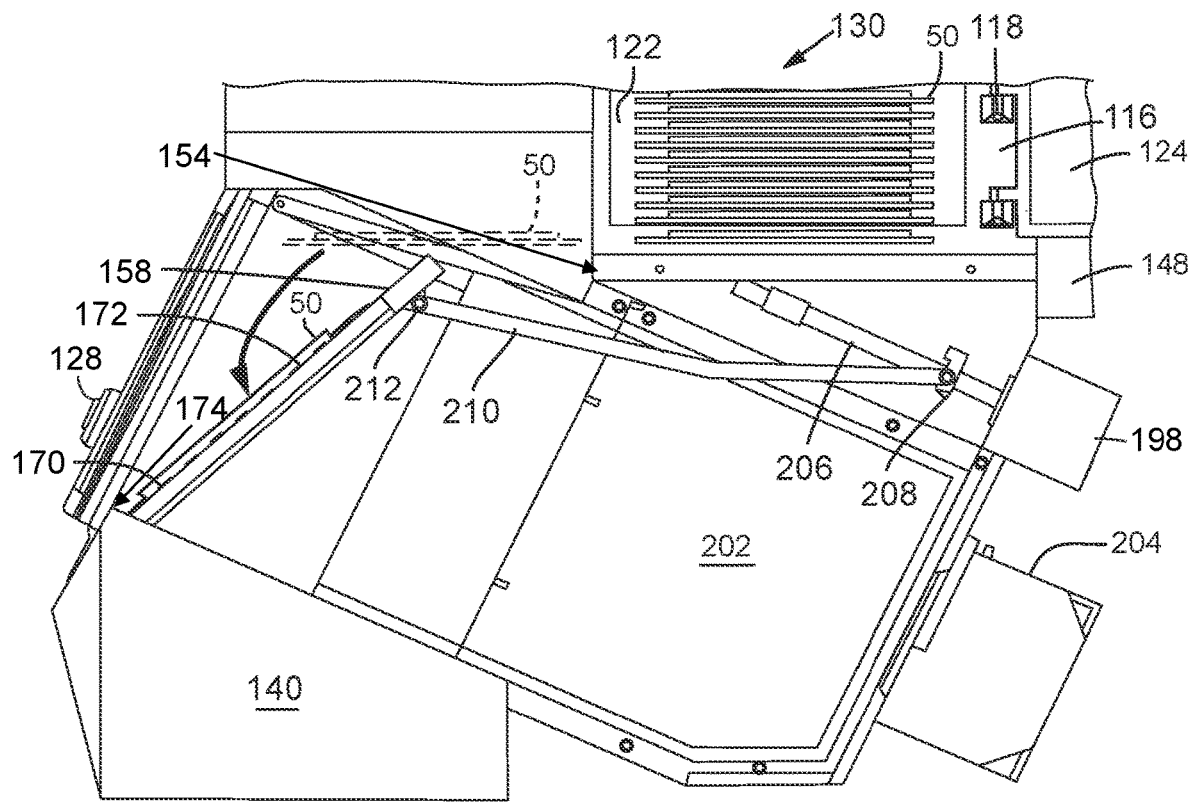
Figure 16D:
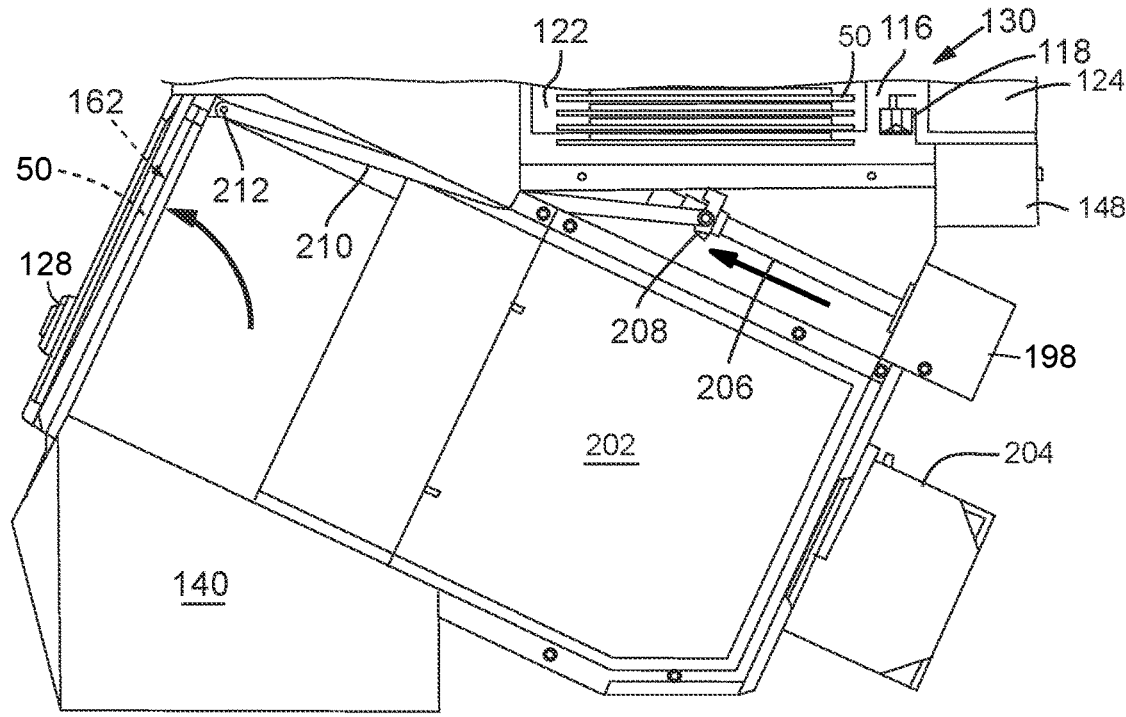
Figure 17A:
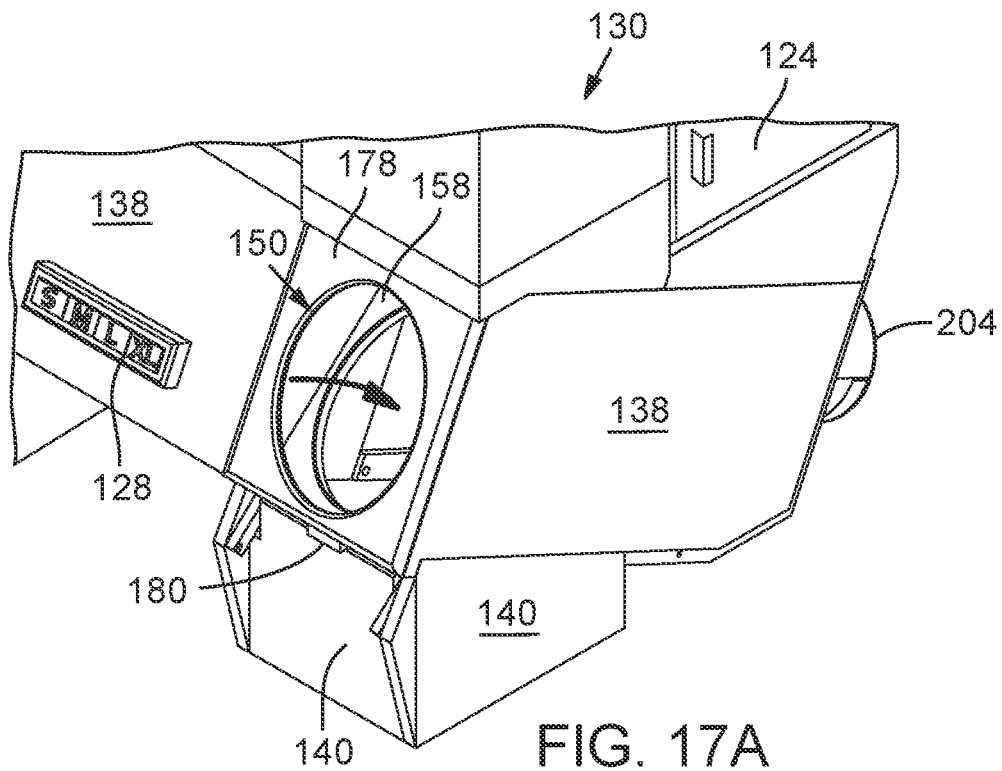
FIGS. 17A and 17B are right front isometric views of a glove-dispensing region of a glove-dispensing system, showing a portion of a cartridge removal sequence.
Figure 17B:
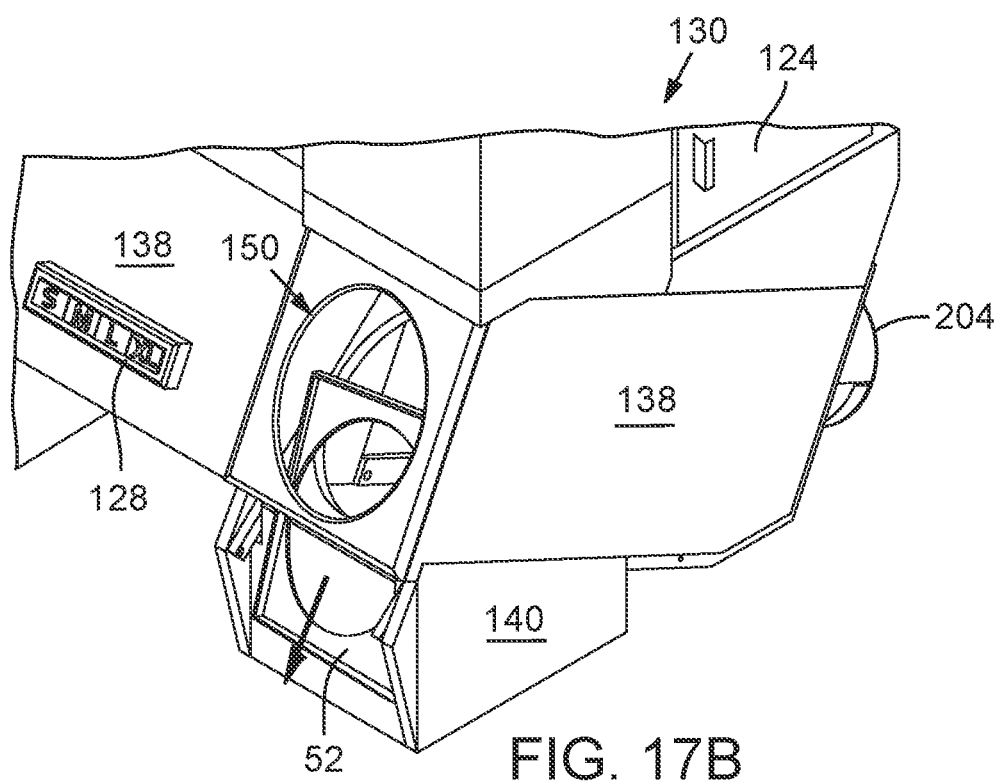

FIG. 15 is a right side cross-sectional view of the glove-dispensing system 130, with portions cut away to show internal components. FIGS. 16A, 16B, 16C, and 16D right side cross-sectional views of a glove-dispensing region of a glove-dispensing system 130, showing an example of part of a sequence for loading glove cartridge 50 into a glove-dispensing position 162 between a sealing plate 158 and a glove portal face 178. FIGS. 17A and 17B are right front isometric views of a glove-dispensing region of the glove-dispensing system 130, showing part of a cartridge removal sequence. One will appreciate that the same sequence would work in connection with the glove-dispensing machine 120.

With reference to FIGS. 11-17B, each cartridge holding chamber 122 may be equipped with a cartridge deck actuator 152 that is configured to move a glove cartridge 50 through a cartridge slot 154 at the base of the holding chamber 122 and into an adjacent cartridge pathway chamber 146 and ultimately onto a sealing plate 158. In one embodiment, as shown in the figures, the cartridge deck actuator 152 may include one or more effectors 156 configured to apply a pushing force to the glove cartridge 50 to move it through the cartridge slot 154. In some embodiments, the cartridge deck actuator 152 may be responsive to a cartridge deck actuator motor 148, such that the cartridge deck actuator motor 148 may be connected to a lead screw which, when spun by the motor 148, drives the effector(s) 156 through a lead screw nut to push the glove cartridge 50 through the cartridge slot 154 toward the cartridge pathway chamber 146 from the holding chamber 122.

One will appreciate that the cartridge deck actuator 152 may alternatively be employed to move the glove cartridge 50 off the top of a stack of glove cartridges 50. Optical or other sensing systems may be used to determine the position of the top glove cartridge 50, or the entire stack may be sensed and moved to position the top glove cartridge 50 in line with the actuator. Moreover, the glove cartridges 50 may be stored vertically side by side, and the cartridge deck actuator 152 may be oriented appropriately.

The upper pathway chambers 146a and 146b may each include one or more cartridge slides 160 that permit the glove cartridges 50 to be directed by gravity onto the sealing plate 158. In this regard, the cartridge slides 160 may be configured with slopes that are steep enough to permit gravity to move the glove cartridges 50 on to the sealing plate 158. The cartridge slides 160 may all be angled in the same direction and at the same slopes, or they may be angled in different directions and/or at different angles. For example, an upper slide 160 may be configured to deliver the glove cartridge 50 at least partly onto or into contact with a lower slide 160.

The slide angles may be configured to retain the glove cartridge 50 in its as loaded (in the holding chamber) face up or face down (or sideways) configuration and its original orientation with respect to its major aperture axis 86. Alternatively, the arrangement of the cartridge slides 160 can be configured to flip and/or rotate the glove cartridge 50 one or more times between the holding chamber 122 and the sealing plate 158.

In some embodiments, a single cartridge deck actuator 152 may be employed to serve all of the holding chambers 122 or each glove-dispensing machine 120. In yet other embodiments, a centralized cartridge moving mechanism can be employed to move the glove cartridges 50 from all of the holding chambers 122 of the glove-dispensing machines 120 on both sides of the glove-dispensing system 130. Such a centralized system may employ a cartridge extraction mechanism utilizing vacuum or other conveyance system.

One will appreciate that the glove cartridges 50 have some similarities in size and shape to computer discs and that automated transport and manipulation of computer discs during their manufacture and use are well known. U.S. Pat. No. 5,335,218, the disclosure of which is incorporated herein by reference, provides a suitable example of how discs can be loaded and conveyed between different locations. The glove-dispensing system 130 need not being wedded to this particular conveying system. However, one can utilize any known disc conveyance technique to move a glove cartridge 50 from its holding chamber 122 to the sealing plate 158. For convenience, the route that the glove cartridges 50 take between the holding chamber 122 and the sealing plate 158 may be called a cartridge path or cartridge pathway.

The sealing plate 158 may be positioned within the lower housing potion 138 and may be angled away from the glove portal 150 such that a bottom 170 of a front surface 172 of the sealing plate 158 is in proximity to a bottom 174 of a rear surface 176 of a glove portal face 178 of the glove portal 150. The bottom 170 and the bottom 174 may be spaced apart when receiving a glove cartridge 50, and a retaining system or device 180, such as a cartridge retaining solenoid or other gate or switch, may be employed to prevent the glove cartridge 50 from passing in between. The retaining device 180 effectively stops the glove cartridge 50 in front of the glove portal 150 of the vacuum chamber 202 and may be configured or programmed to allow the glove cartridge 50 to drop below once the glove 20 has been removed from the glove cartridge 52.

The sealing plate 158 may have a sealing plate aperture 182, and the sealing plate 158 and sealing plate aperture 182 may have any shapes, such as elliptical, oval, circular, or polygonal. Possible polygonal shapes may include, but are not limited to, rectangular, square, pentagonal, hexagonal, octagonal, or dodecagonal. The shapes do not have to correspond; however, the perimeter of the sealing plate 158 will be greater than the perimeter of the sealing plate aperture 182.

The sealing plate aperture 182 may have a major aperture dimension along a major aperture axis that is greater than or equal to the major aperture dimension 80 of the cartridge 52 so that the sealing plate does impede a hand 190 (FIG. 18B) from reaching into the glove 20. However, one will appreciate that if the major aperture dimension 80 is sufficiently large, then the major aperture dimension of the sealing plate aperture 182 may be smaller than the major aperture dimension 80. The major axis of the sealing plate aperture 182 may be aligned to that of the cartridge aperture 58, or they may have different alignments.

Similarly, the glove portal face 178 and the glove portal 150 may have any shapes, such as elliptical, oval, circular, or polygonal. Possible polygonal shapes may include, but are not limited to, rectangular, square, pentagonal, hexagonal, octagonal, or dodecagonal. The shapes do not have to correspond; however, the perimeter of the glove portal face 178 will be greater than the perimeter of the glove portal 150. The glove portal face 178 may employ a transparent, semi-transparent, or translucent material, or may include one or more windows of such materials. Such embodiments would permit a user to see the gloves 20 beyond the glove portal face 178. Visual confirmation that the gloves are in a spread out or hand-receiving configuration, as later discussed, may be useful.

The glove portal 150 may have a major aperture dimension 192 along a major aperture axis 194 and a minor aperture axis 196, wherein the major aperture axis 194 is greater than or equal to the major aperture dimension of the sealing plate 158 so that the glove portal face 178 cannot impede a hand 190 from reaching through the sealing plate 158. However, one will appreciate that the major aperture dimension 192 of the glove portal 150 may be smaller than the major aperture dimension of the sealing plate 158. The major axis 194 of the sealing plate aperture 182 may be aligned to that of sealing plate aperture 182, or they may have different alignments.

In many embodiments, the cartridge aperture 58 is smaller than or equal to the glove portal 150 and smaller than or equal to the sealing plate 158. In particular, the major aperture dimension 80 of the cartridge aperture 58 may be smaller than or equal to the major aperture dimension 192 of the glove portal 150 and smaller than or equal to the major aperture dimension sealing plate 158.

Based on its selected orientation in the holding chamber 122, the glove cartridge 50 may be conveyed step by step to the sealing plate 158 in a known desirable orientation. Alternatively, edge or boundary configurations or features on the glove cartridge 50 can be physically or optically analyzed so that the orientation of the glove cartridge 50 can be manipulated or corrected at or before reaching the sealing plate 158. In some embodiments, the glove cartridge 50 may be oriented so that the thumb is toward the top of the glove portal 150 such as aligned with vertical axis. For example, as previously mentioned, the major opening axis 44 of the glove 20 may be aligned with the major aperture axis of the cartridge 52. However, the glove cartridge 50 may be oriented so that the thumb of the glove is offset from the vertical axis, in which case either or both of the major opening axis 44 of the glove 20 and the major aperture axis of the cartridge 52 may be offset with respect to the vertical axis (and may be offset with respect to each other at a glove-orientation angle as previously described).

After the glove cartridge 50 is moved from the holding chamber 122 and seated on the sealing plate 158, a sealing plate actuator 200 may be employed to press the glove cartridge 50 against a front surface (such as the back surface 176 of the glove portal face) of a vacuum chamber 202 that may be, or include part of, the lower housing portion 138.

In one embodiment, the sealing plate actuator 200 employs a sealing plate actuator motor 198 that utilizes a ball-screw assembly. In particular, the sealing plate actuator motor 198 may have a ball screw 206 attached to it which, when spun, causes a ball nut 208 to move along the ball screw 206. The ball nut 208 may be connected to a drive arm 210 that may be connected to the sealing plate 158 such that spinning of the motor 198 causes movement of the sealing plate. The drive arm 210 may be straight, bent, or curved and the connections may be immobile or pivoted such as through one or more pivot assemblies 212. One will appreciate, however, that the sealing plate actuator 200 could be a cam-operated system, mechanical-path system, or any type of other actuation system.

The seal established by the force of the sealing plate actuator 200 between the glove cartridge 50 and the back surface 176 may be substantially airtight and/or hermetic. An O-ring seal may be used, such as with an O-ring on each side of the cartridge. Alternatively or additionally, O-ring gaskets may be positioned around on one or more of the sealing plate aperture 182 on the sealing plate 158 and the glove portal 150 on the back surface 176 of the glove portal face 178. A flexible sealing membrane that seals between the cartridge sealing plate 158 and vacuum chamber 202 may alternatively or additionally be employed. Such a flexible membrane would allow the sealing plate 158 to move relative to the vacuum chamber 202 during cartridge loading. In other embodiments, the flat major surface 48 of the cartridge 52 may directly contact the back surface 176 of the glove portal face 178 without a gasket.

The aperture ridge 62 of the cartridge 52 generally has a height that is greater than the thickness of the cartridge 52. So, if the aperture ridge 62 of the cartridge 52 faces away from the sealing plate 158, then the aperture ridge 62 may protrude through the glove portal 150. If the aperture ridge 62 of the cartridge 52 faces toward the sealing plate 158, then the aperture ridge 62 may protrude through the sealing plate aperture 182.

One will appreciate that a glove-dispensing system 130 employing two glove-dispensing machines 120 may provide the glove portal faces 178 of both machines 120 so that they lie along the same plane. However, the planes of the glove portal faces 178 of the two machines 120 may be angled with respect to each other. Moreover, these angles may lie along two axes or three axes. One will also appreciate that the cartridges 52 may be positioned over the two glove portals so that the major opening axes 44 of the gloves 20 are substantially parallel. However, the cartridges 52 may be positioned over the two glove portals so that the major opening axes 44 of the gloves 20 are at an angle. In such embodiments, selected side edges of the two cartridge frame boundaries 56 may be parallel with the major opening axes 44 at angles with respect to the major aperture axes 82 of the cartridges 52 and with respect to each other. However, the major opening axes 44 may be parallel or colinear with the major aperture axes 82 of the cartridges 52, and the selected side edges of the two cartridge frame boundaries 56 may be positioned at an angle to each other.

The vacuum chamber 202 may be connected directly or indirectly to a vacuum source 204 to create a vacuum pressure within the vacuum chamber 202. The vacuum source 204 may be automated to turn on after the vacuum chamber 202 is sealed. The vacuum pressure is set at a level sufficient to pull the upper region 22, the middle region 24, and the lower region 26 of the glove 20 away from the glove portal 150, effectively spreading open the tubes of the finger parts 28, palm part 30, thumb part 34, and wrist part 36 without disconnecting the glove base 38 from the aperture ridge 62. The vacuum pressure effectively causes the glove 20 to assume a spread out or hand-receiving configuration that facilitates placement of a hand 190 into the glove 20 as later described. One will appreciate that the vacuum pressure may also be sufficient to break any tear lines 112 that would otherwise prevent the glove 20 from expanding.

One will also appreciate that the vacuum chamber 202 may be capable of containing positive pressure as well as vacuum pressure. The vacuum source 204 may have a reversible capability to provide the vacuum chamber 202 with positive pressure, or the glove-dispensing machine may include a separate positive pressure source as well as a vacuum source 204.

Once the hand 190 is inserted into the glove 22, the pressure in the vacuum chamber 202 may be changed from a vacuum pressure to positive pressure. Positive pressure may help force the glove 20 onto the inserted hand 190 and may also help disconnect ("pop") the glove base 38 off of the aperture ridge 62. A pressure sensor may be used to regulate the chamber vacuum/pressure. Pressure employed in the vacuum chamber 202 may depend on a variety of variables including, but not limited to, the sizes (or relative sizes) of the cartridge aperture 58 and the glove portal 150 and the material and elasticity of the gloves 20. Pressure may be in the range of +/−14 kPa (2 psi), +/−7 kPa (1 psi), +/−3.5 kPa (0.5 psi), or +/−1.7 kPa (0.25 psi). Many embodiments utilize the +/−3.5 kPa (0.5 psi) range.

After the glove 20 has been removed from the glove cartridge 50, the empty cartridge 52 can be discarded through a bottom of the vacuum chamber 202 and collected in a bin that may be positioned in the base 140 beneath and/or in front of the lower housing portion 138. One or more sensors may establish that the glove 20 has been removed from the cartridge 52 and communicate directly or indirectly (such as through a central controller) with a vacuum controller to turn off the vacuum source 204 or reverse the flow to create positive pressure in the vacuum chamber to reduce or prevent outside air from coming into the vacuum chamber 202.

After removal of the vacuum pressure or the creation of positive pressure, the sealing plate actuator 200 may be instructed to eliminate force against the empty cartridge 52 and return to a relaxed, receiving configuration. Then, the retaining device 180 may be instructed to permit the empty cartridge 52 to pass through the gateway and fall into the bin. The cartridge disposal bin may be integrated into the glove-dispensing system 130 or be a separate standard bin. Finally, the retaining device 180 closes the gateway, and the sealing plate 158 is ready to receive a new glove cartridge 50, when a glove size is selected. One will appreciate that the cartridge removal steps can be conducted after a glove size is selected; however, to improve throughput, one will appreciate that it may be preferable to have the sealing plate 158 in a ready to receive state as the standby state.

Figure 18A:
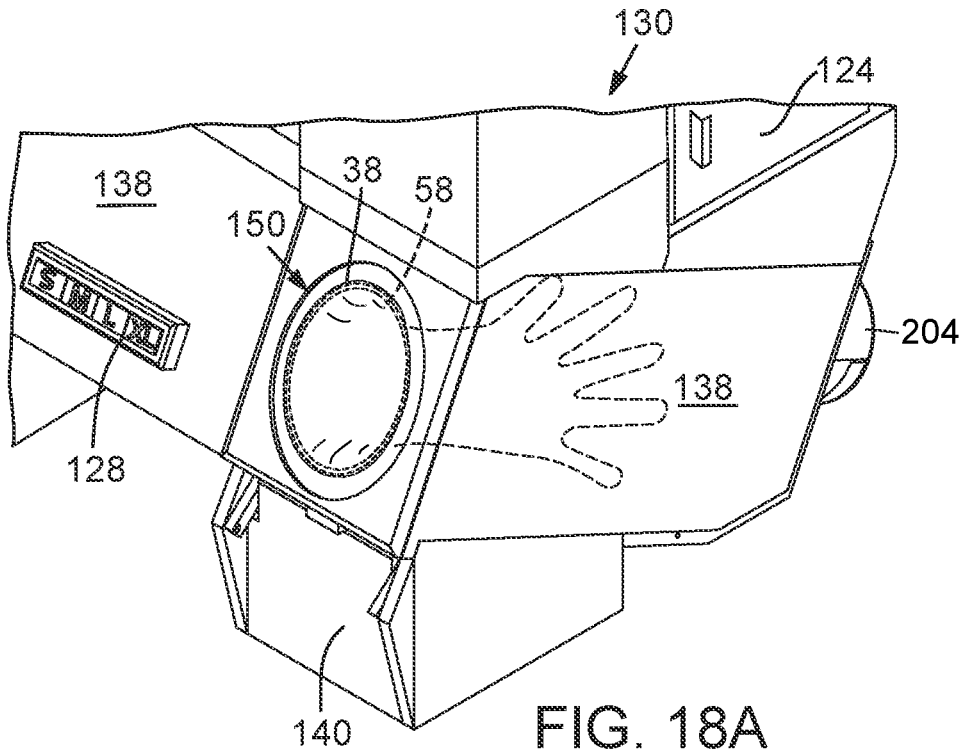
FIGS. 18A-18C are right front isometric views of a glove-dispensing region of a glove-dispensing system, showing an example of a portion of a sequence for placing a glove onto a hand, including positioning a hand through a dispenser aperture and through a cartridge aperture of a glove cartridge to receive a glove.
Figure 18B:
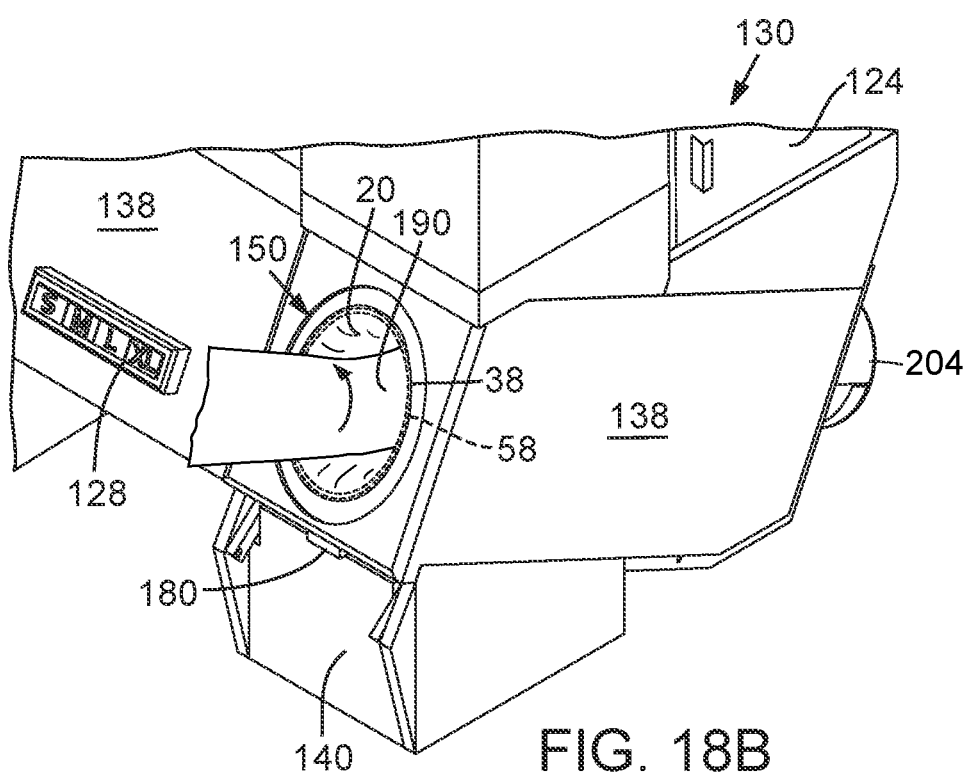
Figure 18C:
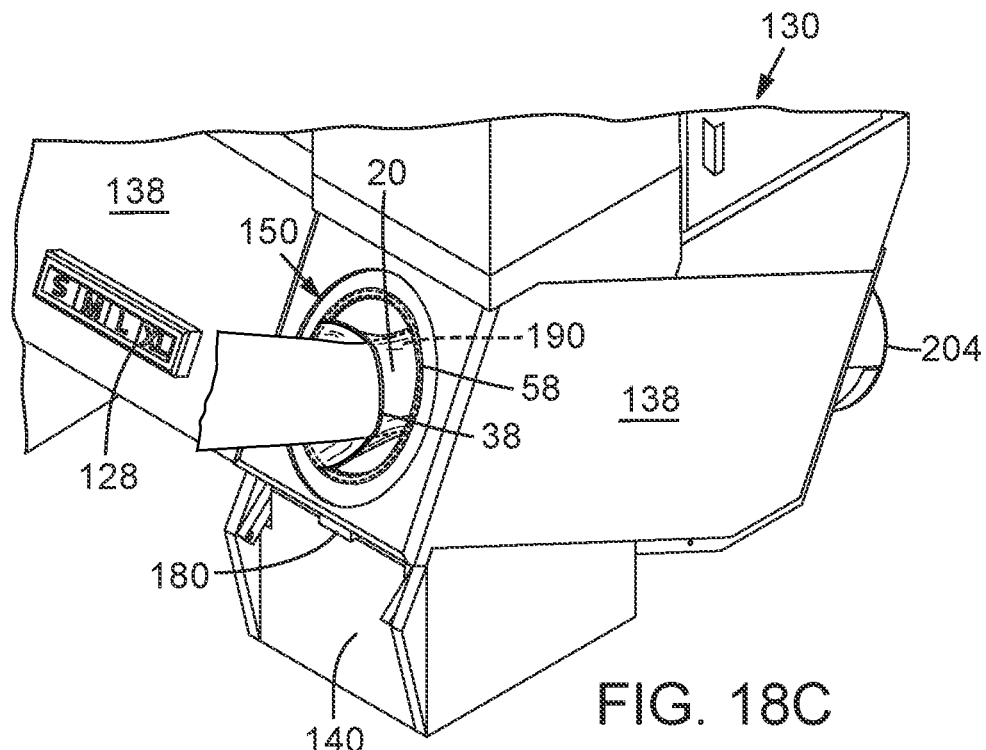
Figure 19:
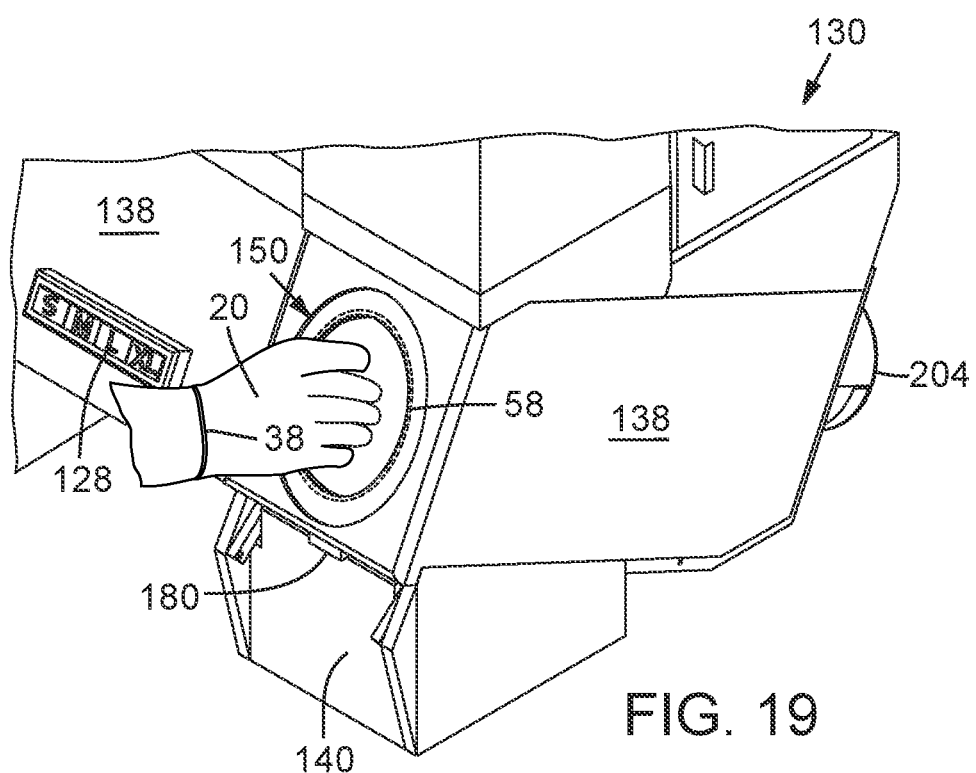
FIG. 19 is an image of a hand covered by a glove dispensed by the glove-dispensing machine of FIGS. 18A-18C.

FIGS. 18A-18C are right front isometric views of a glove-dispensing region of a glove-dispensing system 130, showing an example of part of a sequence for placing a glove 20 onto a hand 190, including positioning the hand 190 through a glove portal 150 and through a cartridge aperture 58 of a glove cartridge 50 to receive the glove 20, and FIG. 19 is an image of a hand 190 covered by the glove 20 that has been dispensed by the glove-dispensing system 130 of FIG. 8. One will appreciate that the same sequence would work in connection with the glove-dispensing machine 120.

With reference to FIGS. 18A-18C and 19, a hand 190 can be easily inserted into a flexible glove 20 of the correct size after the vacuum pressure has been supplied from the vacuum source 204. The glove parts, particularly the finger parts 28, are spread wide by the vacuum pressure, and the hand 190 can readily enter the glove 20, even if the hand 190 is recently washed and not completely dry.

After the hand 190 is inserted into the glove 20 to the depth and fit of a user's satisfaction, the user can use a twist of the hand or arm to release the glove base 38 from the aperture ridge 62, which consequently releases the glove 20 from the glove cartridge 50. With respect to hand movements, an easy movement is to go from a thumb-up direction and rotating the hands inward (anatomical internal rotation) so the thumbs are pointing at each other. Then pulling the hands outward (away from the system 130). Accordingly, the glove-dispensing system 130 may be configured to orient the glove cartridge 50 at the back surface 176 of the glove portal face 178 (or on the sealing plate 158) so that the thumb is toward the top.

One or more sensors, as previously described, can shut the vacuum (and supply positive pressure) so that the hand 190 bearing the glove 20 can be extracted from the glove-dispensing system 130. Alternatively, as previously discussed, positive pressure may be employed earlier to help force the glove 22 onto the inserted hand 190 and help disconnect the glove base 38 from of the aperture ridge 62. In some embodiments, a slight twist of the hand 190, combined with the positive pressure in the chamber, allows for the glove 20 to be removed from the cartridge 52 with ease. One will also appreciate that positive pressure may be employed to disconnect the glove base 38 from of the aperture ridge 62 without any assistance from the hand 190. One will appreciate that two glove-dispensing machines 120 can operate to provide gloves 20 to two hands simultaneously or sequentially. One will appreciate that a single glove-dispensing machine 120 can operate to provide gloves 20 to two hands sequentially, or that two adjacent single glove-dispensing machines 120 can operate to provide gloves 20 to two hands sequentially simultaneously or sequentially.

With reference to FIG. 10, the glove-dispensing machine 120 or the glove-dispensing system 130 may be configured to be wall mounted. Such machine 120 or system 130 may be configured with or without a base 140. However, it may have any of the features previously described.

With reference again to FIGS. 7-19, in some embodiments, a glove-dispensing system 130 that includes two glove-dispensing machines 120 that share common components, such as previously described with respect to certain components, to store, select, and convey a selected set of gloves 20 (individually or as a pair) to the respective glove portals 150. Common components may include, but are not limited to, one or more of: the size selector panel 128, the size selector mechanism(s) 126, the cartridge pathway chamber 146, the cartridge deck actuators 152, the sealing plate actuator 200, the vacuum chamber 202, and the vacuum source 204. Some or all of these shared common components may be centrally located, such as vertically and/or horizontally between or partly between the glove portals 150.

In some embodiments, a glove-dispensing machine 120 may be configured with two glove portals 150 that are spaced close to each other, and any of the previously described components can be configured to store and convey glove cartridges 50 that have two cartridge apertures 58, each supporting a glove 20. Alternatively, the glove-dispensing machine 120 may be configured with single larger glove portal 150 that is large enough to accommodate two hands 190.

Figure 20:
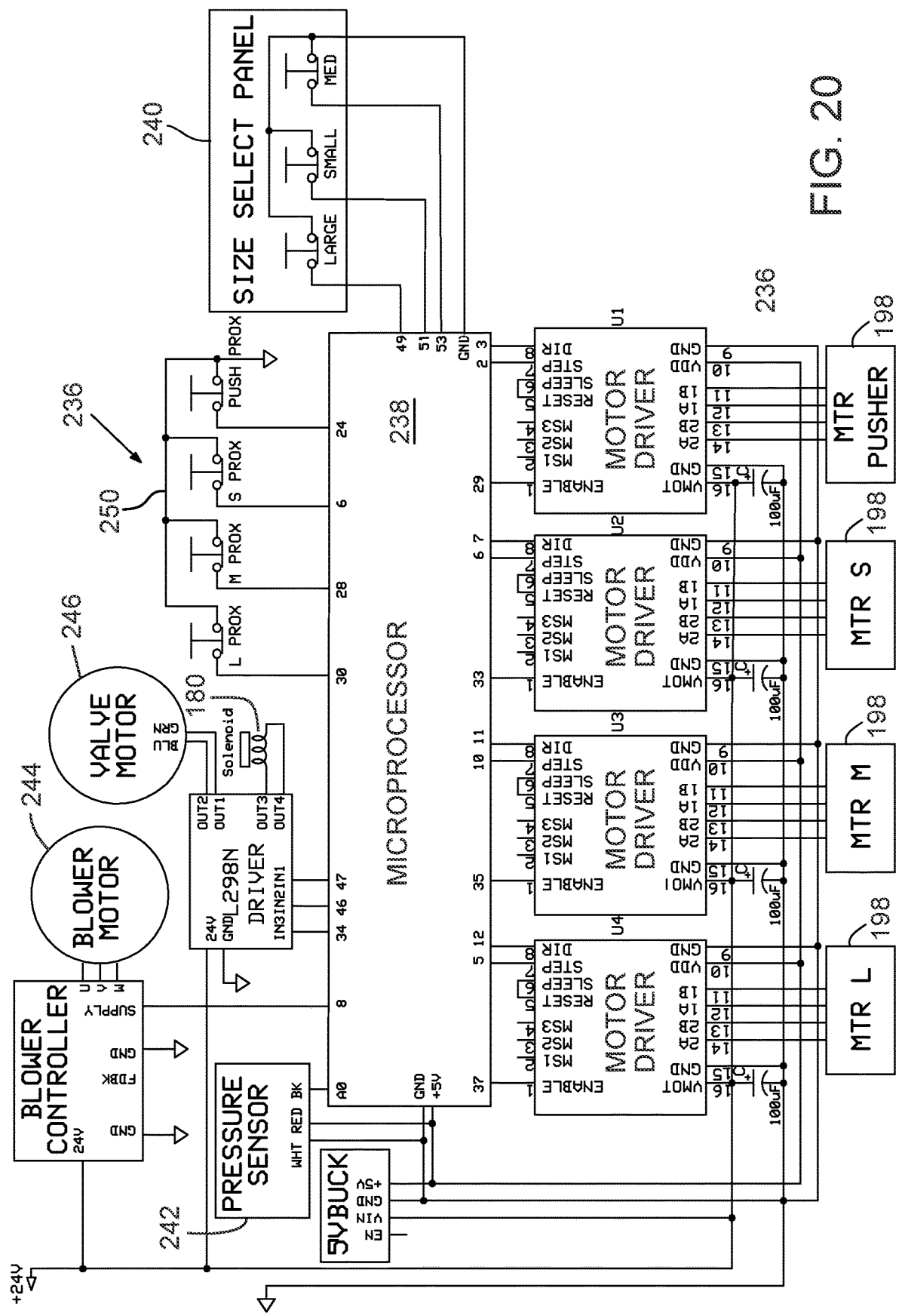
FIG. 20 is a schematic diagram of example circuitry that can be employed to facilitate operation of a glove-dispensing machine.

FIG. 20 is a schematic diagram of example circuitry 236 that can be employed to facilitate operation of a glove-dispensing machine 120 or a glove-dispensing system 130. The entire system 130 (or machine 120) may be powered by directly plugging it into a standard wall outlet. One will appreciate that the system 130 or machine 120 can be readily adapted through conventional converters to run off of solar or low-voltage systems if the need arises.

With reference to FIG. 20, the circuitry 236 may employ a microprocessor controller 238. The circuitry 236 may be employed to control and/or respond to embodiments of the size selector mechanisms 126, such as non-contact size selection buttons. In one embodiment, multi-color status LEDs may be arranged in a circle around each size selection button to indicate which button is being pressed, including a "progression ring" system. When the hand 190 is placed near the size selection, the LED's light up in a progression fashion around the selection, until they make a complete circle, indicating that size selection has been detected. The LED ring may also indicate whether the machine is low on glove cartridges or out of glove cartridges or whether there is a jam in the machine, by changing colors and/or blinking in deterministic patterns.

The cartridge deck actuators 152 may also be controlled by the circuitry 236. Proximity sensors, such as, limit switches 250, may be employed at the end of travel for each control motor, such as the cartridge deck actuator motors 148, to detect when desired movement, such as distance of travel, has been completed. Sensors may also be employed to detect that the actuation of cartridge through the glove-dispensing machine 120 has been completed successfully, including loading and unloading from in front of the vacuum chamber 202.

A detection mechanism may be employed to make sure that the correct size glove cartridge 50 has been loaded in front of the vacuum chamber 202 to warn the user and/or eject the cartridge 50 if it is not the size selected. As noted earlier, the glove cartridges 50 may include indicia, such as RFID tags, that can easily convey size and other information about the gloves 20 or cartridges 50.

Other motors, such as for the vacuum source 204, may also be controlled by the circuitry 236. The vacuum source 204, such as a blower motor 244, used to generate vacuum may be variable speed and may be controlled using a closed-loop system with a pressure sensor 242 mounted inside the vacuum chamber 202 for the feedback.

A detection method may be employed for safety purposes to determine whether a hand 190 has been inserted, so the glove-dispensing machine 120 does not actuate in an unsafe way while the hand 190 is inside it. Moreover, sensors may also be employed to detect when the user has inserted their hand(s) 190 into the glove(s) 20, either independently or collectively, which may trigger an automatic reversal of vacuum into pressure to help remove the glove base(s) 38 from the aperture ridges(s) 62. Moreover, an air switch, such as a valve motor 246, may be employed to change the direction of airflow, to either build up vacuum in the vacuum chamber 202 to inflate the glove(s) 20, or to reverse the blower motor 244 and/or release the pressure to force the glove base(s) 38 from the aperture ridges(s) 62 of the glove cartridge(s) 50 once the hand or hands 190 are inserted.

Figure 21A:
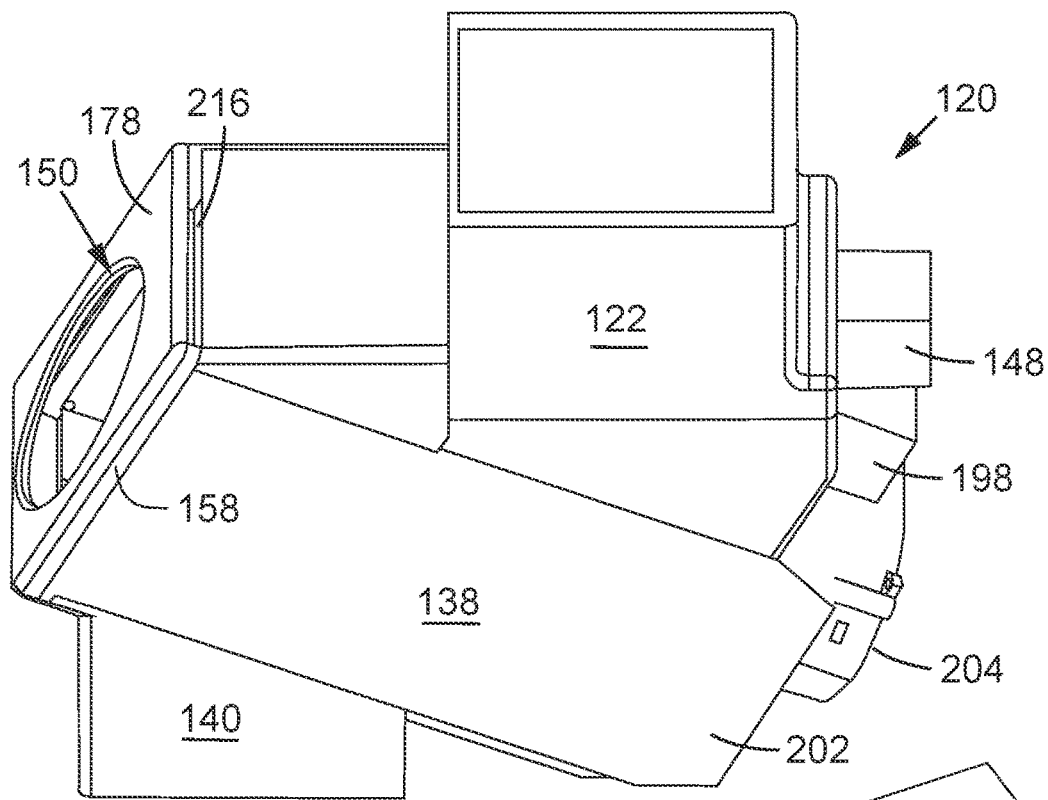
FIG. 21A is a top right front isometric view of another embodiment of a glove-dispensing machine that includes an additional manual-feed cartridge slot for glove cartridges.
Figure 21B:
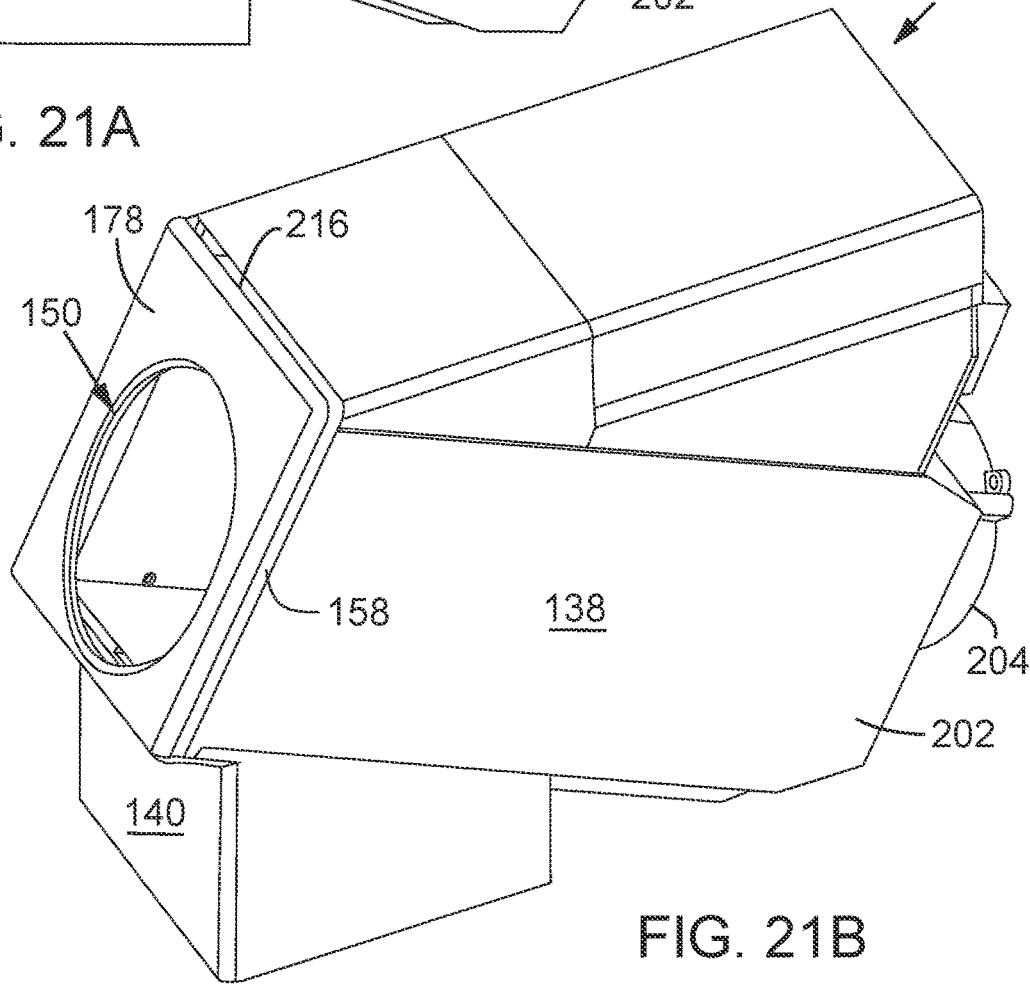
FIG. 21B is a top right front isometric view of another embodiment of a glove-dispensing machine that employs a manual-feed cartridge slot that may replace an automated cartridge feeding system (and optionally excludes cartridge storage chambers).

FIGS. 21A and 21B are top right front isometric views of additional embodiments of glove-dispensing machines 120 that include an additional manual-feed cartridge slot 216 that may replace an automated cartridge feeding system (and may optionally exclude cartridge storage chambers). The manual-feed cartridge slot 216 may be positioned above and behind the glove portal face 178 and above and in front of the sealing plate 158 so that gravity may cause a glove cartridge 50 placed in the slot 216 to slide between the glove portal face 178 and the sealing plate 158. Employing a manual-feed cartridge slot 216 instead of an automated systems could substantially reduce the cost and size of the glove-dispensing machines 120.

The manual-feed cartridge slot 216 may be optionally included in a machine 120 or system 130 that includes the automated feeding mechanism and/or storage chambers 122. The manual-feed cartridge slot 216 may permit a user to insert atypical sizes or specialized gloves 20 that are not dispersed by from the storage chambers 122 by the automated cartridge-feeding system. Sensors could be employed to indicate to the automated cartridge-feeding system that a glove cartridge 50 is already loaded so that the system does not try to provide an extra cartridge 50. The manual-feed cartridge slot 216 could also be employed if any of the cartridge deck actuators 152 are malfunctioning.

Figure 22A:
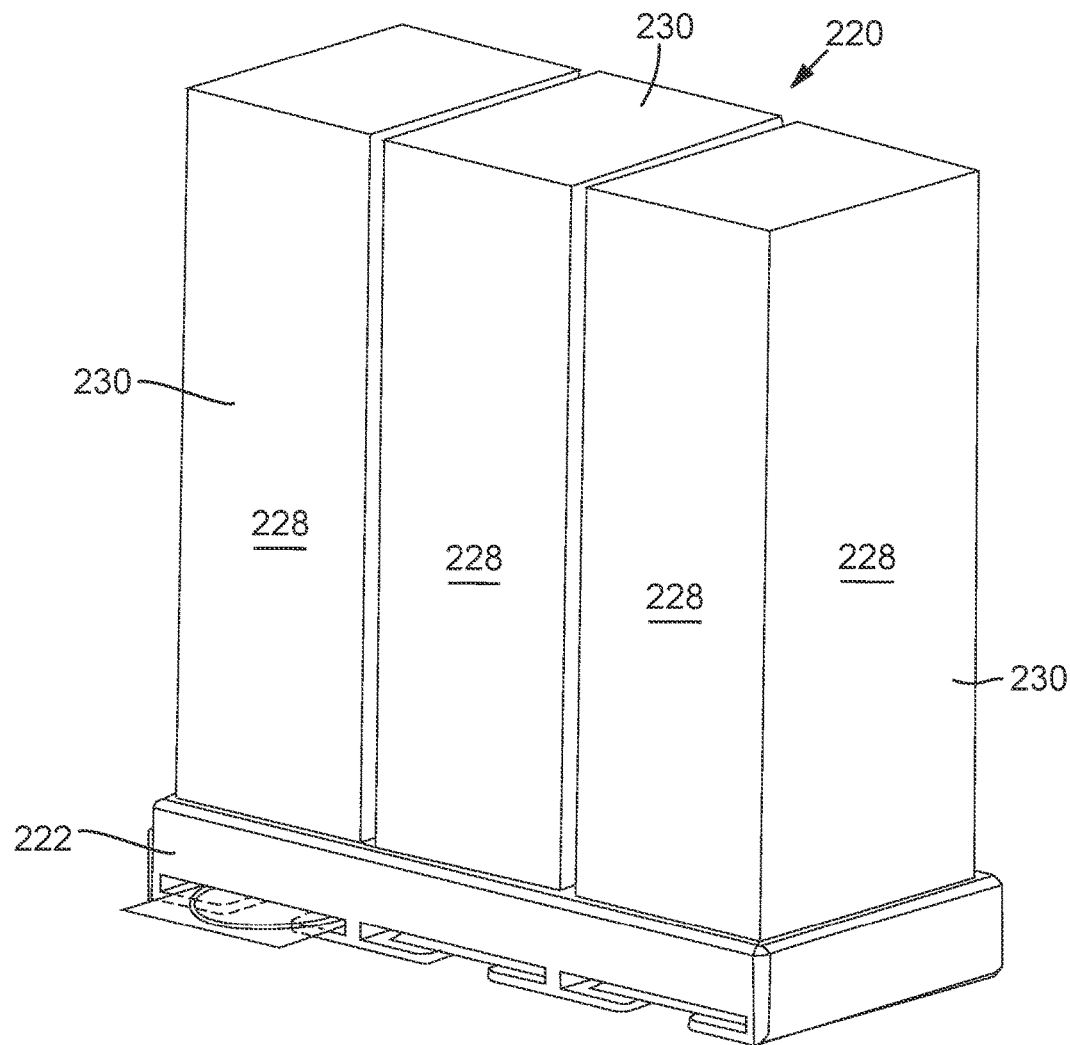
FIG. 22A is a front right isometric view of an example of a stand-alone cartridge storage system.
Figure 22B:
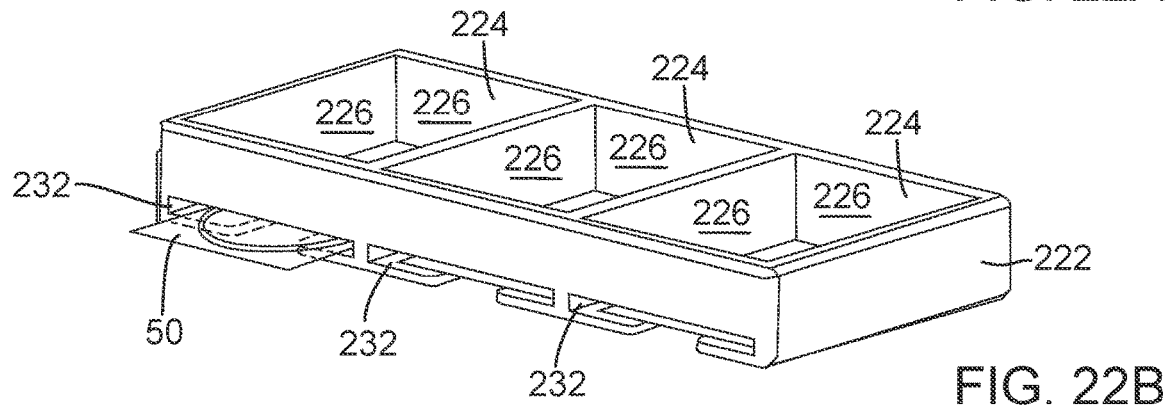
FIG. 22B is a front right isometric view of an example of a bottom frame of a stand-alone cartridge storage system with bottom-dispensing slots.

FIG. 22A is a front right isometric view of an example of a stand-alone cartridge storage system 220 that includes a bottom-dispensing frame 222, and FIG. 22B is a front right isometric view of an example of the bottom-dispensing frame 222. With reference to FIGS. 22A and 22B, the bottom-dispensing frame 222 may include one or more cartridge box receptacles 224 having receptacle walls 226 with length dimensions that match dimensions of box walls 228 of cartridge boxes 230 that each contain multiple glove cartridges 50, such as 50, 100, or 200 glove cartridges 50.

The bottom-dispensing frame 222 may include one or more bottom-dispensing cartridge slots 232. The glove cartridges 50 may be manually dispensed through the slots 232. In some embodiments, the glove cartridges 50 are spring loaded into cartridge boxes 230 to deliver the cartridges downward and/or outward such as via a manual switch or button. Alternatively or additionally, the bottom-dispensing frame 222 may be spring loaded to deliver the glove cartridges 50 outwardly in response to a manual button or switch. The bottom-dispensing frame 222 may be configured for wall mounting, for mounting on the machine 120 or system 130, or for resting on a surface.

FIG. 23 is a front right isometric view of a portion of an example glove-dispensing machine 120 having a slot-insertion storage chamber 122a that may be employed with or without a chamber door 124. The slot-insertion storage chamber 122 may include a slot storage cavity that is dimensioned to confine multiple stacked cartridges 50. A cartridge-insertion slot 234 may be positioned at the top of the cavity to permit glove cartridges 50 to be inserted manually.

Figure 24:
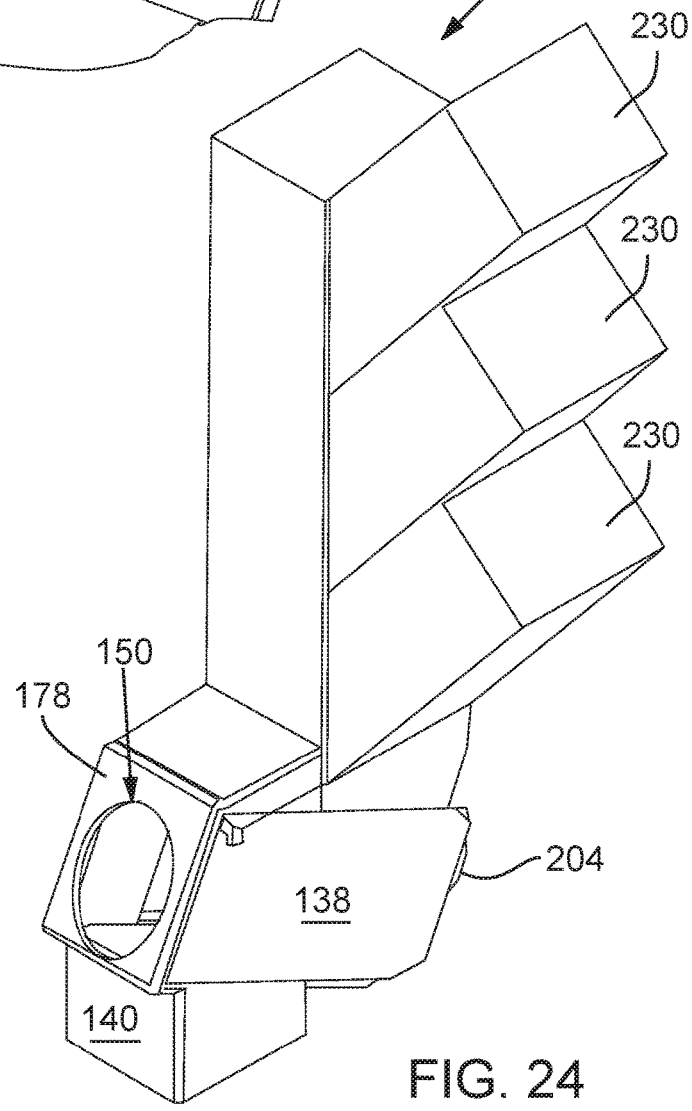
FIG. 24 is top right front isometric view of an example glove-dispensing machine configured for receiving cartridge boxes of multiple cartridges that can be fed directly by an actuator into a cartridge pathway chamber.

FIG. 24 is top right front isometric view of an example glove-dispensing machine 120 configured for receiving cartridge boxes 230 having multiple glove cartridges 50 that can be fed directly from the boxes 230 by one or more actuators 152 into a cartridge pathway chamber 146. The cartridge boxes 230 may be angle downwardly as shown, or they may be positioned vertically or horizontally. Alternatively, high-capacity holding chambers 122 could be integrated into the example glove-dispensing machine 120. Either of these embodiments could eliminate on-site manual transfer and handling of the glove cartridges 50 from the cartridge boxes 230 to the holding chambers 122, eliminating a possible source of contamination.

Figure 25A:
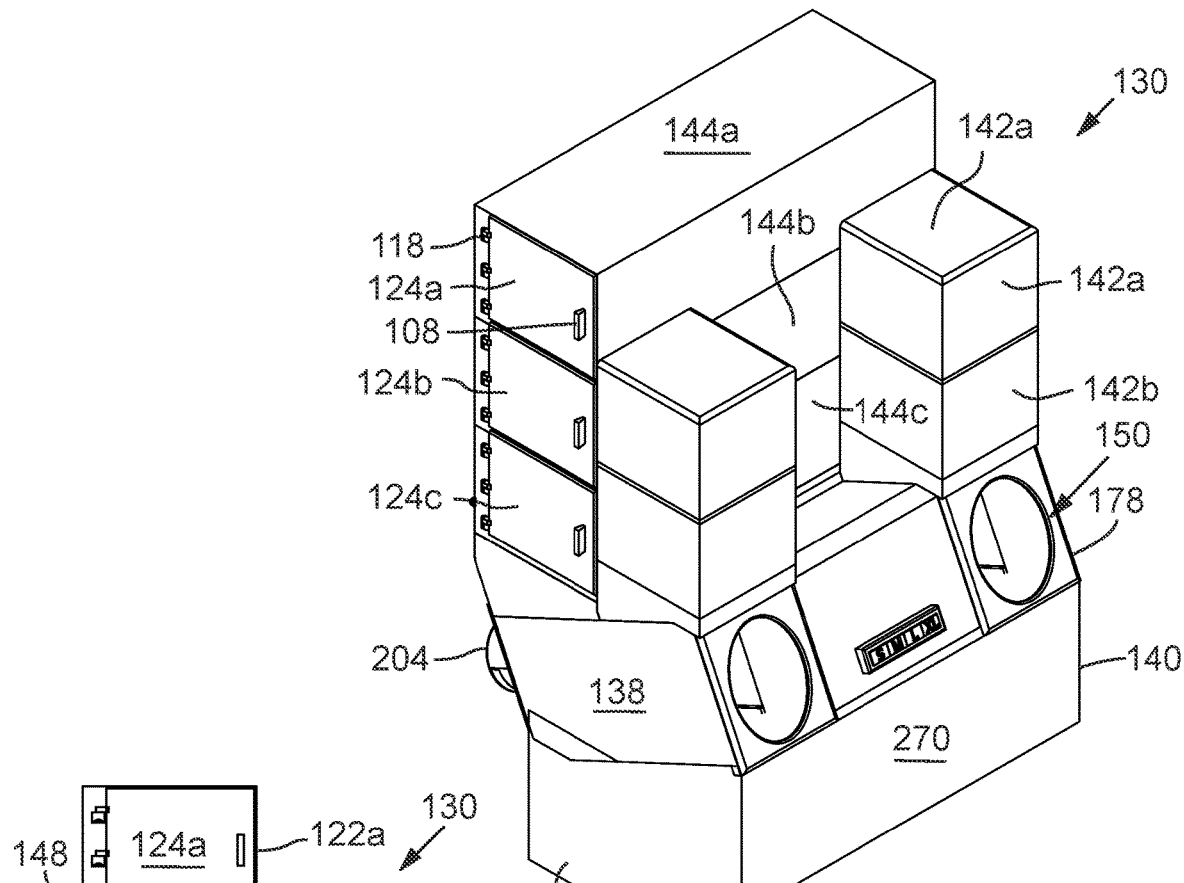
FIG. 25A is a top, left, and front isometric view of an alternative embodiment of a glove-dispensing system including a discard storage chamber for empty cartridges.
Figure 25B:
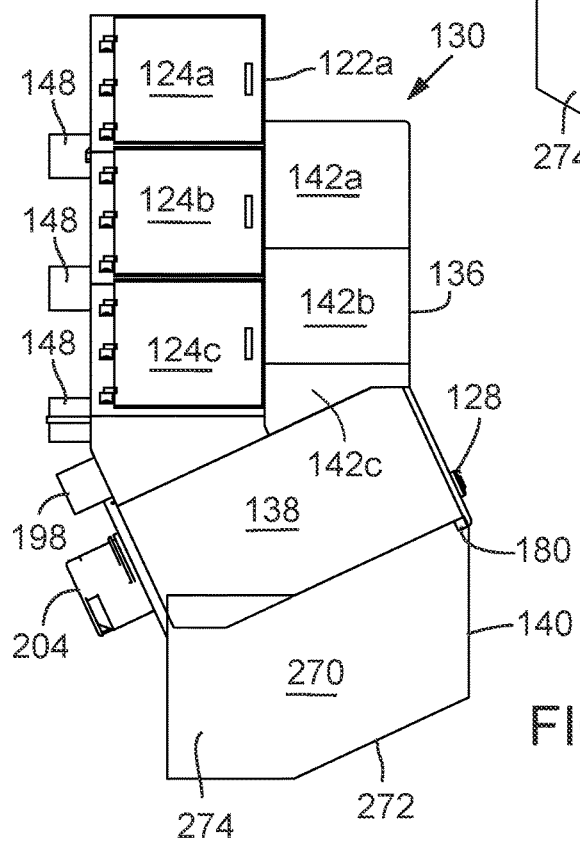
FIG. 25B is a left side view of an alternative embodiment of a glove-dispensing system including a discard storage chamber for empty cartridges.

FIG. 25A is a top, left, and front isometric view of an alternative embodiment of a glove-dispensing system 130 including a discard storage chamber 270 for empty cartridges 52, and FIG. 25B is a left side view of an alternative embodiment of a glove-dispensing system 130 including a discard storage chamber 270 for empty cartridges 52. With reference to FIGS. 25A and 25B, the base 140 of the glove-dispensing system 130 may be enlarged to provide a discard storage chamber 270 which may include a sloped bottom surface 272 to permit discarded cartridges 52 to slide to a collection area 274 away from where they are permitted to fall by release of the retaining device 180. A door (not shown) may be provided to provide easy access to the collection area 244.

CONCLUSION

One will appreciate that the subject matter of any sentence or paragraph can be combined with subject matter of some or all of the other sentences or paragraphs, except where such combinations are mutually exclusive.

The terms and descriptions used above are set forth by way of illustration and example only and are not meant as limitations. Those skilled in the art will recognize that many variations, enhancements, and modifications of the concepts described herein are possible without departing from the underlying principles of the invention.

The scope of the invention should therefore be determined only by the following claims, claims presented in a continuation patent application, and equivalents to the foregoing claims.

The invention claimed is:

1. A glove-dispensing system, comprising:
    a slot configured to receive a glove cartridge, the glove cartridge containing a glove attached around a cartridge aperture that is through a cartridge frame;
    a glove portal face having a rear surface;
    a glove portal configured to allow entry of a hand through the glove portal face and the rear surface;
    a sealing plate configured to apply a glove cartridge against the rear surface of the glove portal face such that glove portal overlaps the cartridge aperture;
    a vacuum chamber that includes the sealing plate; and
    a vacuum source in communication with the vacuum chamber.

2. A glove-dispensing system of claim 1, further comprising one or more holding chambers configured to house multiple glove cartridges, each of the glove cartridges containing a glove attached around a cartridge aperture that is through a cartridge frame.

3. A glove-dispensing system of claim 2, further comprising a cartridge pathway chamber between the holding chamber and the sealing plate.

4. A glove-dispensing system of claim 2, further comprising multiple holding chambers.

5. A glove-dispensing system of claim 2, further comprising multiple holding chambers, including first and second holding chambers configured for holding glove cartridges containing different sizes of gloves.

6. A glove-dispensing system of claim 2, further comprising a cartridge deck actuator that is operable to move a glove cartridge to the cartridge pathway chamber.

7. A glove-dispensing system of claim 2, further comprising a glove size-selector mechanism that presents indicators of different glove sizes, including first and second glove sizes, that are available for selection, wherein the glove size-selector mechanism is configured to directly or indirectly communicate with a cartridge deck actuator that is operable to move a glove cartridge that contains a glove of a selected size to the cartridge pathway chamber.

8. A glove-dispensing system of claim 2, wherein the glove portal has a glove portal area that is greater than or equal to a cartridge aperture area of the cartridge aperture.

9. A glove-dispensing system of claim 2, wherein the sealing plate has a sealing plate aperture that is configured to be aligned with the glove portal whenever the sealing plate applies the glove cartridge against the rear surface of the glove portal face, wherein the sealing plate aperture is configured to allow entry of a hand through the sealing plate.

10. A glove-dispensing system of claim 2, further comprising a sealing plate actuator that is configured to apply force to the sealing plate to move the sealing plate toward the rear surface of the glove portal face.

11. A glove-dispensing system of claim 2, wherein the holding chamber is configured to hold glove cartridges in a first orientation, wherein the cartridge pathway chamber is configured to retain the first orientation of the glove cartridge.

12. A glove-dispensing system of claim 2, wherein the holding chamber is configured to hold glove cartridges in a first orientation, wherein the cartridge pathway chamber is configured to change the first orientation of the glove cartridge to a second orientation that is different from the first orientation.

13. A glove-dispensing system of claim 2, wherein the holding chamber is a primary holding chamber, wherein the glove portal face is a primary glove portal face, wherein the glove portal is a primary glove portal, wherein the sealing plate is a primary sealing plate, wherein the cartridge pathway chamber is a primary cartridge pathway chamber, wherein the vacuum chamber is a primary vacuum chamber, and wherein the vacuum source is a primary vacuum source, the glove-dispensing system further comprising:
one of more of a secondary holding chamber, a secondary glove portal face, a secondary glove portal, a secondary sealing plate, a secondary cartridge pathway chamber, a secondary vacuum chamber, and a secondary vacuum source.

14. A glove-dispensing system of claim 13, further comprising: a secondary vacuum chamber, wherein the secondary vacuum chamber is connected to the secondary glove portal, and wherein the primary vacuum chamber is connected to the primary glove portal.

15. A glove-dispensing system of claim 13, wherein the vacuum source is connected to the primary and secondary vacuum chambers.

16. A glove-dispensing system of claim 13, further comprising: a secondary vacuum source that is connected to the secondary vacuum chamber, and wherein the primary vacuum source is connected to the primary vacuum chamber.

17. A glove-dispensing system of claim 1, wherein the glove-dispensing system is configured to be mounted on a wall without additional support from a ground surface.

18. A glove-dispensing system of claim 1, wherein the vacuum chamber is connected to a source of positive pressure.

19. A glove-dispensing system of claim 1, wherein the vacuum source is configured to cooperate with the vacuum chamber and a glove cartridge to inflate a glove on the glove cartridge.

20. A glove-dispensing system of claim 1, wherein the vacuum source is configured to cooperate with the vacuum chamber and a glove cartridge to stretch at least one finger part of the glove on the glove cartridge.

21. A glove-dispensing system of claim 1, wherein the vacuum source is configured to cooperate with the vacuum chamber and a glove cartridge to stretch a middle region of the glove on the glove cartridge.

22. A glove-dispensing system of claim 1, wherein the glove portal face is a primary glove portal face, and wherein the glove portal is a primary glove portal, the glove-dispensing system further comprising:
a secondary glove portal that is through a secondary glove portal face, wherein the secondary glove portal face lies in a secondary plane that is different from primary plane of the primary glove portal face.

23. A glove-dispensing system of claim 1, wherein the glove cartridges are primary glove cartridges, wherein the glove is a primary glove, wherein the cartridge aperture is a primary cartridge aperture, wherein the cartridge frame is a primary cartridge frame, wherein the glove portal is a primary glove portal that is through a primary portal face and a primary back surface of the primary portal face, the glove-dispensing system further comprising:
a secondary glove portal that is through a secondary portal face and a secondary back surface of the secondary portal face; and
secondary glove cartridges, each of the glove cartridges containing a secondary glove attached around a secondary cartridge aperture that is through a secondary cartridge frame, wherein the primary glove has a primary major opening axis, wherein the secondary glove has a secondary major opening axis, wherein the primary cartridge aperture has a primary aperture axis, wherein the secondary cartridge aperture has a secondary aperture axis, wherein the primary major opening axis has a primary relationship with the primary aperture axis, wherein the secondary major opening axis has a secondary relationship with the secondary aperture axis, and wherein the glove-dispensing system in cooperation with the primary and secondary relationships is configured to apply the primary and secondary glove cartridges to the respective primary and secondary back surfaces of the respective primary and secondary glove portal faces so that the primary major opening axis is transverse to the secondary major opening axis.

24. A glove-dispensing system of claim 1, wherein the holding chamber is a first primary holding chamber that is configured to hold multiple first glove cartridges having first gloves of a first size, wherein the glove portal face is a primary glove portal face, wherein the glove portal is a primary glove portal, wherein the rear surface is a primary rear surface, where in the glove portal face is a primary glove portal face, wherein the sealing plate is a primary sealing plate, wherein the cartridge pathway chamber is a primary cartridge pathway chamber, wherein the vacuum chamber is a primary vacuum chamber, and wherein the vacuum source is a primary vacuum source, the glove-dispensing system further comprising:
a second primary holding chamber that is configured to hold multiple second glove cartridges having second gloves of a second size that is different from the first size;
an optional first secondary holding chamber that is configured to hold multiple first glove cartridges having first gloves of the first size;
an optional second secondary holding chamber that is configured to hold multiple second glove cartridges having second gloves of the second size;
an optional secondary sealing plate, an optional secondary cartridge pathway chamber, an optional secondary vacuum chamber, and an optional secondary vacuum source;
a secondary rear surface of a secondary glove portal face and a secondary glove portal that is through the secondary rear surface of the secondary glove portal face;
a glove size-selector mechanism that presents indicators of first and second glove sizes that are available for selection, wherein the glove size-selector mechanism is configured to directly or indirectly communicate with one or more cartridge actuators that are operable to move two respective first or second glove cartridges that correlate with a selected size at the glove size-selector mechanism, wherein the glove-dispensing system is operable to convey the two selected first or second glove cartridges to be applied to the primary and secondary rear surfaces of the respective primary and secondary glove portals.

25. A glove-dispensing system of claim 1, comprising:
a primary holding chamber configured to house primary multiple glove cartridges, each of the primary glove cartridges containing a primary glove attached around a primary cartridge aperture that is through a primary cartridge frame;
a primary glove portal face having a primary rear surface;
a primary glove portal configured to allow entry of a primary hand through the primary glove portal face and the primary rear surface;
a primary sealing plate configured to apply a glove cartridge against the primary rear surface of the primary glove portal face such that primary glove portal overlaps the primary cartridge aperture;
a primary cartridge pathway chamber between the primary holding chamber and the primary sealing plate;
a primary vacuum chamber that includes the primary sealing plate; and
a primary vacuum source in communication with the primary vacuum chamber;
a secondary holding chamber configured to house secondary multiple glove cartridges each of the secondary glove cartridges containing a secondary glove attached around a secondary cartridge aperture that is through a secondary cartridge frame;
a secondary glove portal face having a secondary rear surface; and
a secondary glove portal configured to allow entry of a secondary hand through the secondary glove portal face and the secondary rear surface.

26. A glove-dispensing system of claim 1, comprising:
a primary glove-dispending machine, including:
 a primary holding chamber configured to house primary multiple glove cartridges each of the primary glove cartridges containing a primary glove attached around a primary cartridge aperture that is through a primary cartridge frame;
 a primary glove portal face having a primary rear surface;
 a primary glove portal configured to allow entry of a primary hand through the primary glove portal face and the primary rear surface;
 a primary sealing plate configured to apply a primary glove cartridge against the primary rear surface of the primary glove portal face such that primary glove portal overlaps the primary cartridge aperture;
 a primary cartridge pathway chamber between the primary holding chamber and the primary sealing plate;
 a primary vacuum chamber that includes the primary sealing plate; and
 a primary vacuum source in communication with the primary vacuum chamber; and
a secondary glove-dispending machine, including:
 a secondary holding chamber configured to house secondary multiple glove cartridges each of the secondary glove cartridges containing a secondary glove attached around a secondary cartridge aperture that is through a secondary cartridge frame;
 a secondary glove portal face having a secondary rear surface;
 a secondary glove portal configured to allow entry of a secondary hand through the secondary glove portal face and the secondary rear surface;
 a secondary sealing plate configured to apply a secondary glove cartridge against the secondary rear surface of the secondary glove portal face such that secondary glove portal overlaps the secondary cartridge aperture;
 a secondary cartridge pathway chamber between the secondary holding chamber and the secondary sealing plate;
 a secondary vacuum chamber that includes the secondary sealing plate; and
 a secondary vacuum source in communication with the secondary vacuum chamber.

27. A glove-dispensing system, comprising:
a primary holding chamber configured to house primary multiple glove cartridges, each of the primary glove cartridges containing a primary glove attached around a primary cartridge aperture that is through a primary cartridge frame;
a primary glove portal face having a primary rear surface;
a primary glove portal configured to allow entry of a primary hand through the primary glove portal face and the primary rear surface;
a primary sealing plate configured to apply a glove cartridge against the primary rear surface of the primary glove portal face such that primary glove portal overlaps the primary cartridge aperture;
a primary cartridge pathway chamber between the primary holding chamber and the primary sealing plate;
a primary vacuum chamber that includes the primary sealing plate; and
a primary vacuum source in communication with the primary vacuum chamber;
a secondary holding chamber configured to house secondary multiple glove cartridges each of the secondary glove cartridges containing a secondary glove attached around a secondary cartridge aperture that is through a secondary cartridge frame;
a secondary glove portal face having a secondary rear surface; and
a secondary glove portal configured to allow entry of a secondary hand through the secondary glove portal face and the secondary rear surface.

28. A glove-dispensing system, comprising:
a primary glove-dispending machine, including:
 a primary holding chamber configured to house primary multiple glove cartridges each of the primary glove cartridges containing a primary glove attached around a primary cartridge aperture that is through a primary cartridge frame;
 a primary glove portal face having a primary rear surface;
 a primary glove portal configured to allow entry of a primary hand through the primary glove portal face and the primary rear surface;
 a primary sealing plate configured to apply a primary glove cartridge against the primary rear surface of the primary glove portal face such that primary glove portal overlaps the primary cartridge aperture;
 a primary cartridge pathway chamber between the primary holding chamber and the primary sealing plate;
 a primary vacuum chamber that includes the primary sealing plate; and
 a primary vacuum source in communication with the primary vacuum chamber; and
a secondary glove-dispending machine, including:
 a secondary holding chamber configured to house secondary multiple glove cartridges each of the secondary glove cartridges containing a secondary glove attached around a secondary cartridge aperture that is through a secondary cartridge frame;

a secondary glove portal face having a secondary rear surface;

a secondary glove portal configured to allow entry of a secondary hand through the secondary glove portal face and the secondary rear surface;

a secondary sealing plate configured to apply a secondary glove cartridge against the secondary rear surface of the secondary glove portal face such that secondary glove portal overlaps the secondary cartridge aperture;

a secondary cartridge pathway chamber between the secondary holding chamber and the secondary sealing plate;

a secondary vacuum chamber that includes the secondary sealing plate; and a secondary vacuum source in communication with the secondary vacuum chamber.

29. A method for facilitating the donning of a glove, comprising:

in response to a size selection signal, conveying from a holding chamber a glove cartridge so that it is positioned adjacent to a glove portal, wherein the glove cartridge contains a glove attached around a cartridge aperture through a cartridge frame, wherein the glove portal provides access to a vacuum chamber;

applying vacuum pressure to the vacuum chamber to expand the glove into the vacuum chamber; and releasing the glove from the glove cartridge onto a hand in response to movement of the hand after it has been inserted into the glove or in response to positive pressure supplied to the vacuum chamber after the hand has been inserted into the glove.

30. A method of claim 29, wherein the method employs a glove-dispensing system to deliver the glove cartridge to the glove portal, wherein the holding chamber has a slot configured to receive the glove cartridge from the holding chamber, wherein the glove portal has a glove portal face having a rear surface, wherein the glove portal is configured to allow entry of a hand through the glove portal face and the rear surface, wherein the vacuum chamber includes a sealing plate configured to apply the glove cartridge against the rear surface of the glove portal face such that the glove portal overlaps the cartridge aperture, and wherein the vacuum chamber is in communication with a vacuum source.

31. A method of claim 29, wherein the holding chamber is a primary holding chamber or a secondary holding chamber, each of which are configured to house multiple glove cartridges, each of the glove cartridges containing a glove attached around a cartridge aperture that is through a cartridge frame, and wherein the glove cartridge is conveyed from the primary holding chamber or the secondary holding chamber.

32. A method of claim 31, wherein the first and second holding chambers are configured for holding glove cartridges containing different sizes of gloves.

33. A method of claim 29, wherein conveying the glove cartridge employs a cartridge deck actuator that is operable to move a glove cartridge to a cartridge pathway chamber for conveying the glove cartridge between the holding chamber and the vacuum chamber.

34. A method of claim 29, wherein the size selection signal originates from a glove size-selector mechanism that presents indicators of different glove sizes, including first and second glove sizes, that are available for selection, wherein the glove size-selector mechanism is configured to directly or indirectly communicate with a cartridge deck actuator that is operable to move a glove cartridge that contains a glove of a selected size to a cartridge pathway chamber.

35. A method of claim 30, wherein the sealing plate has a sealing plate aperture that is configured to be aligned with the glove portal whenever the sealing plate applies the glove cartridge against the rear surface of the glove portal face, wherein the sealing plate aperture is configured to allow entry of a hand through the sealing plat, and wherein a sealing plate actuator is configured to apply force to the sealing plate to move the sealing plate toward the rear surface of the glove portal face.

36. A method of claim 29, wherein the holding chamber is configured to hold glove cartridges in a first orientation, wherein a cartridge pathway chamber for conveying the glove cartridge between the holding chamber and the vacuum chamber is configured to retain the first orientation of the glove cartridge.

37. A method of claim 29, wherein the holding chamber is configured to hold glove cartridges in a first orientation, wherein a cartridge pathway chamber for conveying the glove cartridge between the holding chamber and the vacuum chamber is configured to change the first orientation of the glove cartridge to a second orientation that is different from the first orientation.

38. A method of claim 30, wherein the holding chamber is a primary holding chamber, wherein the glove portal face is a primary glove portal face, wherein the glove portal is a primary glove portal, wherein the sealing plate is a primary sealing plate, wherein the cartridge pathway chamber is a primary cartridge pathway chamber, wherein the vacuum chamber is a primary vacuum chamber, wherein the vacuum source is a primary vacuum source, wherein the glove-dispensing system further comprises:

one of more of a secondary holding chamber, a secondary glove portal face, a secondary glove portal, a secondary sealing plate, a secondary cartridge pathway chamber, a secondary vacuum chamber, and a secondary vacuum source.

39. A method of claim 38, wherein the glove-dispensing system comprises a secondary vacuum chamber, wherein the secondary vacuum chamber is connected to the secondary glove portal, and wherein the primary vacuum chamber is connected to the primary glove portal.

40. A method of claim 38, wherein the vacuum source is connected to the primary and secondary vacuum chambers.

41. A method of claim 38, wherein the glove-dispensing system comprises a secondary vacuum source that is connected to the secondary vacuum chamber, and wherein the primary vacuum source is connected to the primary vacuum chamber.

42. A method of claim 29, wherein the method employs a glove-dispensing system to deliver the glove cartridge to the glove portal, and wherein the glove-dispensing system is configured to be mounted on a wall without additional support from a ground surface.

43. A method of claim 30, wherein the glove portal face is a primary glove portal face, wherein the glove portal is a primary glove portal, and wherein the glove-dispensing system further comprises:

a secondary glove portal that is through a secondary glove portal face, wherein the secondary glove portal face lies in a secondary plane that is different from primary plane of the primary glove portal face.

44. A method of claim 30, wherein the glove cartridge is primary glove cartridge, wherein the glove is a primary glove, wherein the cartridge aperture is a primary cartridge aperture, wherein the cartridge frame is a primary cartridge frame, wherein the glove portal is a primary glove portal that is through a primary portal face and a primary back surface of the primary portal face, and wherein the glove-dispensing system further comprises:
- a secondary glove portal that is through a secondary portal face and a secondary back surface of the secondary portal face; and
- secondary glove cartridges, each of the glove cartridges containing a secondary glove attached around a secondary cartridge aperture that is through a secondary cartridge frame, wherein the primary glove has a primary major opening axis, wherein the secondary glove has a secondary major opening axis, wherein the primary cartridge aperture has a primary aperture axis, wherein the secondary cartridge aperture has a secondary aperture axis, wherein the primary major opening axis has a primary relationship with the primary aperture axis, wherein the secondary major opening axis has a secondary relationship with the secondary aperture axis, and wherein the glove-dispensing system in cooperation with the primary and secondary relationships is configured to apply the primary and secondary glove cartridges to the respective primary and secondary back surfaces of the respective primary and secondary glove portal faces so that the primary major opening axis is transverse to the secondary major opening axis.

45. A method of claim 30, wherein the holding chamber is a first primary holding chamber that is configured to hold multiple first glove cartridges having first gloves of a first size, wherein the glove portal face is a primary glove portal face, wherein the glove portal is a primary glove portal, wherein the rear surface is a primary rear surface, where in the glove portal face is a primary glove portal face, wherein the sealing plate is a primary sealing plate, wherein the cartridge pathway chamber is a primary cartridge pathway chamber, wherein the vacuum chamber is a primary vacuum chamber, wherein the vacuum source is a primary vacuum source, and wherein the glove-dispensing system further comprises:
- a second primary holding chamber that is configured to hold multiple second glove cartridges having second gloves of a second size that is different from the first size;
- an optional first secondary holding chamber that is configured to hold multiple first glove cartridges having first gloves of the first size;
- an optional second secondary holding chamber that is configured to hold multiple second glove cartridges having second gloves of the second size;
- an optional secondary sealing plate, an optional secondary cartridge pathway chamber, an optional secondary vacuum chamber, and an optional secondary vacuum source;
- a secondary rear surface of a secondary glove portal face and a secondary glove portal that is through the secondary rear surface of the secondary glove portal face;
- a glove size-selector mechanism that presents indicators of first and second glove sizes that are available for selection, wherein the glove size-selector mechanism is configured to directly or indirectly communicate with one or more cartridge actuators that are operable to move two respective first or second glove cartridges that correlate with a selected size at the glove size-selector mechanism, wherein the glove-dispensing system is operable to convey the two selected first or second glove cartridges to be applied to the primary and secondary rear surfaces of the respective primary and secondary glove portals.

46. A method of claim 30, wherein the glove-dispensing system comprises:
- a primary holding chamber configured to house primary multiple glove cartridges, each of the primary glove cartridges containing a primary glove attached around a primary cartridge aperture that is through a primary cartridge frame;
- a primary glove portal face having a primary rear surface;
- a primary glove portal configured to allow entry of a primary hand through the primary glove portal face and the primary rear surface;
- a primary sealing plate configured to apply a glove cartridge against the primary rear surface of the primary glove portal face such that primary glove portal overlaps the primary cartridge aperture;
- a primary cartridge pathway chamber between the primary holding chamber and the primary sealing plate;
- a primary vacuum chamber that includes the primary sealing plate; and
- a primary vacuum source in communication with the primary vacuum chamber;
- a secondary holding chamber configured to house secondary multiple glove cartridges each of the secondary glove cartridges containing a secondary glove attached around a secondary cartridge aperture that is through a secondary cartridge frame;
- a secondary glove portal face having a secondary rear surface; and
- a secondary glove portal configured to allow entry of a secondary hand through the secondary glove portal face and the secondary rear surface.

47. A method of claim 30, wherein the glove-dispensing system comprises:
- a primary glove-dispending machine, including:
  - a primary holding chamber configured to house primary multiple glove cartridges each of the primary glove cartridges containing a primary glove attached around a primary cartridge aperture that is through a primary cartridge frame;
  - a primary glove portal face having a primary rear surface;
  - a primary glove portal configured to allow entry of a primary hand through the primary glove portal face and the primary rear surface;
  - a primary sealing plate configured to apply a primary glove cartridge against the primary rear surface of the primary glove portal face such that primary glove portal overlaps the primary cartridge aperture;
  - a primary cartridge pathway chamber between the primary holding chamber and the primary sealing plate;
  - a primary vacuum chamber that includes the primary sealing plate; and
  - a primary vacuum source in communication with the primary vacuum chamber; and
- a secondary glove-dispending machine, including:
  - a secondary holding chamber configured to house secondary multiple glove cartridges each of the secondary glove cartridges containing a secondary glove attached around a secondary cartridge aperture that is through a secondary cartridge frame;
  - a secondary glove portal face having a secondary rear surface;

a secondary glove portal configured to allow entry of a secondary hand through the secondary glove portal face and the secondary rear surface;
a secondary sealing plate configured to apply a secondary glove cartridge against the secondary rear surface of the secondary glove portal face such that secondary glove portal overlaps the secondary cartridge aperture;
a secondary cartridge pathway chamber between the secondary holding chamber and the secondary sealing plate;
a secondary vacuum chamber that includes the secondary sealing plate; and
a secondary vacuum source in communication with the secondary vacuum chamber.

* * * * *